United States Patent
Zwirn

(10) Patent No.: US 11,096,672 B2
(45) Date of Patent: *Aug. 24, 2021

(54) CLUTTER SUPPRESSION IN ULTRASONIC IMAGING SYSTEMS

(71) Applicant: CRYSTALVIEW MEDICAL IMAGING LIMITED, St. Helier (GB)

(72) Inventor: Gil Zwirn, Moshav Mazor (IL)

(73) Assignee: CRYSTALVIEW MEDICAL IMAGING LTD.

( * ) Notice: Subject to any disclaimer, the term of this patent is extended or adjusted under 35 U.S.C. 154(b) by 749 days.

This patent is subject to a terminal disclaimer.

(21) Appl. No.: 15/656,031

(22) Filed: Jul. 21, 2017

(65) Prior Publication Data

US 2019/0021700 A1    Jan. 24, 2019

(51) Int. Cl.
*A61B 8/08* (2006.01)
*G01S 15/89* (2006.01)
(Continued)

(52) U.S. Cl.
CPC ............ *A61B 8/5269* (2013.01); *A61B 8/145* (2013.01); *A61B 8/4444* (2013.01); *A61B 8/4488* (2013.01); *A61B 8/4494* (2013.01); *G01S 7/52077* (2013.01); *G01S 15/8927* (2013.01); *G01S 15/8981* (2013.01);
(Continued)

(58) Field of Classification Search
CPC ............ G01S 7/52077; G01S 15/8997; G01S 15/8927; G01S 15/8981; G01S 7/52095; G01S 7/52038

See application file for complete search history.

(56) References Cited

U.S. PATENT DOCUMENTS 5,224,174 A * 6/1993 Schneider ........... G01S 7/52061
382/124
5,410,208 A    4/1995 Walters et al.
(Continued)

FOREIGN PATENT DOCUMENTS

GB    2502997    9/2014

OTHER PUBLICATIONS

Cai, R. Statistical Characterization of the Medical Ultrasound Echo Signals. Sci Rep 6, 39379 (2016). https://doi.org/10.1038/srep39379 (Year: 2016).*

(Continued)

*Primary Examiner* — Amanda Lauritzen Moher
*Assistant Examiner* — Jillian K. McGough
(74) *Attorney, Agent, or Firm* — Fresh IP PLC; Clifford D. Hyra; Aubrey Y. Chen

(57) ABSTRACT

Methods and systems for suppressing clutter effects in ultrasonic imaging systems are presented. Two or more receive beams with different and distinct beam patterns are employed for each reception boresight and each reception phase center. The clutter suppression processing is applied to the beamformed data, and is based on computing one or more features for each range-gate. These features may include variability features, providing an estimate of the variability of the signal received by the different elements of the transducer array for the range-gate, and/or derivative/slope features that are an estimation of a function of spatial derivatives of the signal received by the different elements of the transducer array for the range-gate.

10 Claims, 8 Drawing Sheets

(51) Int. Cl.
G01S 7/52 (2006.01)
A61B 8/14 (2006.01)
A61B 8/00 (2006.01)

(52) U.S. Cl.
CPC ....... *G01S 15/8997* (2013.01); *G01S 7/52038* (2013.01); *G01S 7/52095* (2013.01)

(56) References Cited

U.S. PATENT DOCUMENTS

| | | | |
|---|---|---|---|
| 6,251,074 | B1 | 6/2001 | Averkiou et al. |
| 8,045,777 | B2 | 10/2011 | Zwirn |
| 8,254,654 | B2 | 8/2012 | Yen et al. |
| 9,451,932 | B2 | 9/2016 | Zwirn |
| 2009/0141957 | A1* | 6/2009 | Yen ............... G01S 15/8977 382/131 |
| 2016/0192907 | A1* | 7/2016 | Zwirn ............. G01S 7/52047 600/443 |
| 2017/0086793 | A1* | 3/2017 | Sato ................ A61B 8/5276 |

OTHER PUBLICATIONS

Ma C, Varghese T. Analysis of 2-d ultrasound cardiac strain imaging using joint probability density functions. Ultrasound Med Biol. 2014;40(6):1118-1132. doi:10.1016/j.ultrasmedbio.2013.12.028 (Year: 2014).*

"Stationary Clutter Rejection in Echocardiography," Ultrasound in Medicine and Biology, vol. 32, 2006, pp. 43-52 by Zwirn and Akselrod.

"Use of Harmonic Imaging without Echocardiographic Contrast to Improve Two-Dimensional Image Quality," American Journal of Cardiology, vol. 82, 1998, pp. 794-799. by Spencer et al.

"Sub-harmonic Generation from Ultrasonic Contrast Agents," Physics in Medicine and Biology, vol. 44, 1999, pp. 681-694. By Krishna et al.

"Improved Estimation of Low Velocities in Color Doppler Imaging by Adapting the Mean Frequency Estimator to the Clutter Rejection Filter," IEEE Transactions on Biomedical Engineering, vol. 43, 1996, pp. 919-927. by Herment et al.

* cited by examiner

CLUTTER SUPPRESSION IN ULTRASONIC IMAGING SYSTEMS

FIELD OF THE INVENTION

The present invention relates generally to ultrasonic imaging systems, e.g., for medical imaging, and particularly to methods and systems for suppressing clutter effects in ultrasonic imaging systems.

BACKGROUND OF THE INVENTION

Ultrasonic medical imaging plays a crucial role in modern medicine, gradually becoming more and more important as new developments enter the market. Some of the most common ultrasound imaging applications are cardiac imaging (also referred to as echocardiography), abdominal imaging, and obstetrics and gynecology. Ultrasonic imaging is also used in various other industries, e.g., for flaw detection during hardware manufacturing.

Ultrasound images often include artifacts, making the analysis and/or diagnosis of these images a task for highly trained experts. One of the most problematic imaging artifacts is clutter, i.e., undesired information that appears in the imaging plane or volume, obstructing data of interest.

One of the main origins of clutter in ultrasonic imaging is effective imaging of objects outside the mainlobe of the probe's beam, also referred to as sidelobe clutter. Such objects may distort the signal associated with certain imaged spatial regions, adding to them signals originating from irrelevant spatial directions. In most cases, objects in the probe's sidelobes cause significant signal distortion if they are highly reflective to ultrasound waves and/or are located in spatial angles for which the probe's sidelobe level is relatively high. For example, in echocardiography, the dominant reflectors outside the probe's mainlobe are typically the ribcage and the lungs.

Another origin of clutter is multi-path reflections, also called reverberations. In some cases, the geometry of the scanned region with respect to the probe, as well as the local reflective characteristics within the scanned region, cause a noticeable percentage of the transmitted energy to bounce back and forth before reaching the probe. As a result, the signal measured for a certain range with respect to the probe may include contributions from other ranges, in addition to the desired range. If the signal emanating from other ranges is associated with highly reflective elements, it may have a significant effect on the image quality.

An even further origin of clutter is aberrations, that is, spatial variations within tissues resulting in local changes in the speed of sound. Any mismatch between the actual speed of sound within the scanned region and the speed of sound assumed by the beamforming processing may cause defocusing and image quality degradation.

A common medical imaging method for enhancing the visibility of the desired ultrasonic information relative to the clutter is administering contrast agents. Such agents enhance the ultrasonic backscatter from blood and aid in its differentiation from surrounding tissues. They are used, for example, to enhance image quality in patients with low echogenicity, a common phenomenon among obese patients. This method is described, for example, by Krishna et al., in a paper entitled "Sub-harmonic Generation from Ultrasonic Contrast Agents," Physics in Medicine and Biology, vol. 44, 1999, pages 681-694.

Using harmonic imaging instead of fundamental imaging, i.e., transmitting ultrasonic signals at a certain frequency and receiving at an integer multiple, for instance 2, of the transmitted frequency, also reduces clutter effects. Spencer et al. describe this method in a paper entitled "Use of Harmonic Imaging without Echocardiographic Contrast to Improve Two-Dimensional Image Quality," American Journal of Cardiology, vol. 82, 1998, pages 794-799.

U.S. Pat. No. 6,251,074, by Averkiou et al., issued on Jun. 26, 2001, titled "Ultrasonic Tissue Harmonic Imaging," describes ultrasonic diagnostic imaging systems and methods which produce tissue harmonic ultrasonic images from harmonic echo components of a transmitted fundamental frequency. Fundamental frequency waves are transmitted by an array transducer to focus at a focal depth. As the transmitted waves penetrate the body, the harmonic effect develops as the wave components begin to focus. The harmonic response from the tissue is detected and displayed, while clutter from fundamental response is reduced by excluding fundamental frequencies.

Moreover, clutter may be reduced using a suitable probe design. U.S. Pat. No. 5,410,208, by Walters et al., issued on Apr. 25, 1995, titled "Ultrasound Transducers with Reduced Sidelobes and Method for Manufacture Thereof," discloses a transducer with tapered piezoelectric layer sides, intended to reduce sidelobe levels. In addition, matching layers disposed on the piezoelectric layer may similarly be tapered to further increase performance. Alternative to tapering the piezoelectric layer, the top electrode and/or the matching layers may be reduced in size relative to the piezoelectric layer such that they generate a wave which destructively interferes with the undesirable lateral wave.

Furthermore, image-processing methods have been developed for detecting clutter-affected pixels in echocardiographic images by means of post-processing. Zwirn and Akselrod present such a method in a paper entitled "Stationary Clutter Rejection in Echocardiography," Ultrasound in Medicine and Biology, vol. 32, 2006, pages 43-52.

Other methods utilize auxiliary receive ultrasound beams. In U.S. Pat. No. 8,045,777, issued on Oct. 25, 2011, titled "Clutter Suppression in Ultrasonic Imaging Systems," Zwirn describes a method for ultrasonic imaging, comprising: transmitting an ultrasonic radiation towards a target; receiving reflections of the ultrasonic radiation from a region of the target in a main reflected signal and one or more auxiliary reflected signals, wherein each one of the reflected signals is associated with a different and distinct beam pattern, wherein all of the reflected signals have an identical frequency; determining a de-correlation time of at least one of: the main reflected signal and the one or more auxiliary reflected signals; applying a linear combination to the main reflected signal and the one or more auxiliary reflected signals, to yield an output signal with reduced clutter, wherein the linear combination comprises a plurality of complex number weights that are being determined for each angle and for each range within the target tissue, wherein each complex number weight is selected such that each estimated reflection due to the clutter is nullified, wherein a reflection is determined as associated with clutter if the determined de-correlation time is above a specified threshold.

U.S. Pat. No. 9,451,932, by Zwirn, issued on Sep. 27, 2016, titled "Clutter Suppression in Ultrasonic Imaging Systems," describes a method of ultrasound imaging including the following steps: transmitting ultrasound radiation towards a target and receiving reflections of the ultrasound radiation from a region of the target in a main reflected signal and one or more auxiliary reflected signals, wherein each one of the reflected signals comprises an input dataset and is associated with a different and distinct beam pattern; compounding the input datasets from the main reflected signal and one or more auxiliary reflected signals, by the use of a compounding function, said compounding function using parameters derived from spatial analysis of the input datasets.

U.S. Pat. No. 8,254,654, by Yen and Seo, issued on Aug. 28, 2012, titled "Sidelobe Suppression in Ultrasound Imaging using Dual Apodization with Cross-Correlation," describes a method of suppressing sidelobes in an ultrasound image, the method comprising: transmitting a focused ultrasound beam through a sub-aperture into a target and collecting resulting echoes; in receive, using a first apodization function to create a first dataset; in receive, using a second apodization function to create a second dataset; combining the two datasets to create combined RF data; calculating a normalized cross-correlation for each pixel; performing a thresholding operation on each correlation value; and multiplying the resulting cross-correlation matrix by the combined RF data.

Further clutter suppression methods are based on analyzing spatial and/or temporal self-similarity within the ultrasound data. G.B. patent 2,502,997, by Zwirn, issued on Sep. 3, 2014, titled "Suppression of Reverberations and/or Clutter in Ultrasonic Imaging Systems," discloses a method for clutter suppression in ultrasonic imaging, the method comprising: transmitting an ultrasonic radiation towards a target medium via a probe; receiving reflections of the ultrasonic radiation from said target medium in a reflected signal via a scanner, wherein the reflected signal is spatially arranged in a scanned data array, which may be one-, two-, or three-dimensional, so that each entry into the scanned data array corresponds to a pixel or a volume pixel (either pixel or volume pixel being collectively a "voxel"), and wherein the reflected signal may also be divided into frames, each of which corresponding to a specific timeframe (all frames being collectively a "cine-loop"); said method being characterized by the following: step 110—computing one or more self-similarity measures between two or more voxels or groups of voxels within a cine-loop or within a processed subset of the cine-loop, so as to assess their self-similarity; step 120—for at least one of: (i) each voxel; (ii) each group of adjacent voxels within the cine-loop or the processed subset of the cine-loop; and (iii) each group of voxels which are determined to be affected by clutter, based on one or more criteria, at least one of which relates to the self-similarity measures computed in step 110, computing one or more clutter parameters, at least one of which also depends on the self-similarity measures computed in step 110; and step 130—for at least one of: (i) each voxel; (ii) each group of adjacent voxels within the cine-loop or the processed subset of the cine-loop; and (iii) each group of voxels which are determined to be clutter affected voxels, based on one or more criteria, at least one of which relates to the self-similarity measures computed in step 110, applying clutter suppression using the corresponding suppression parameters.

An additional class of currently available methods for handling clutter is a family of clutter rejection algorithms, used in color-Doppler flow imaging. These methods estimate the flow velocity inside blood vessels or cardiac chambers and suppress the effect of slow-moving objects, using the assumption that the blood flow velocity is significantly higher than the motion velocity of the surrounding tissue. These methods are described, for example, by Herment et al. in a paper entitled "Improved Estimation of Low Velocities in Color Doppler Imaging by Adapting the Mean Frequency Estimator to the Clutter Rejection Filter," IEEE Transactions on Biomedical Engineering, vol. 43, 1996, pages 919-927.

SUMMARY OF THE INVENTION

Embodiments of the present invention provide methods and devices for suppressing clutter effects in ultrasonic imaging systems.

According to a first aspect of the invention there is provided a method of ultrasound imaging, said method comprising generating one or more transmit beams towards a target region; defining one or more reception phase centers ("defined reception phase centers"), and for each of said one or more defined reception phase centers defining one or more reception boresights ("defined reception boresights"); for each of said one or more defined reception phase centers, for each of said one or more defined reception boresights, generating two or more receive beams using a probe (26) comprising a transducer array (30), wherein each of said two or more receive beams uses the corresponding defined reception phase center and the corresponding defined reception boresight, and wherein each of said two or more receive beams is associated with a different and distinct beam pattern; for each receive beam, producing beamformed range-gate data; and processing said beamformed range-gate data, said processing comprising, for at least one of said one or more defined reception phase centers, for at least one of said one or more defined reception boresights: (a) for one or more range-gates, computing one or more variability features and/or one or more derivative/slope features (the variability features and derivative/slope features are collectively referred to as "clutter suppression features"), being functions of said beamformed range-gate data associated with at least one of said two or more receive beams, wherein a variability feature for a range-gate is an estimate of the variability of the signal received by the different elements of transducer array (30) for the range-gate, and wherein a derivative/slope feature for a range-gate is an estimate of a function of spatial derivatives of the signal received by the different elements of transducer array (30) for the range-gate, wherein the spatial derivatives are applied along one or more axes of the probe (26) and/or along the range axis; and (b) for each of said one or more range-gates, computing a metric value, wherein said metric value depends on values of one or more of said one or more clutter suppression features for the range-gate.

Other aspects of the present invention are detailed in the claims.

BRIEF DESCRIPTION OF THE DRAWINGS

The invention for clutter suppression in ultrasonic imaging systems is herein described, by way of example only, with reference to the accompanying drawings.

With specific reference now to the drawings in detail, it is emphasized that the particulars shown are by way of example and for purposes of illustrative discussion of the embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF EMBODIMENTS

Figure 1A:
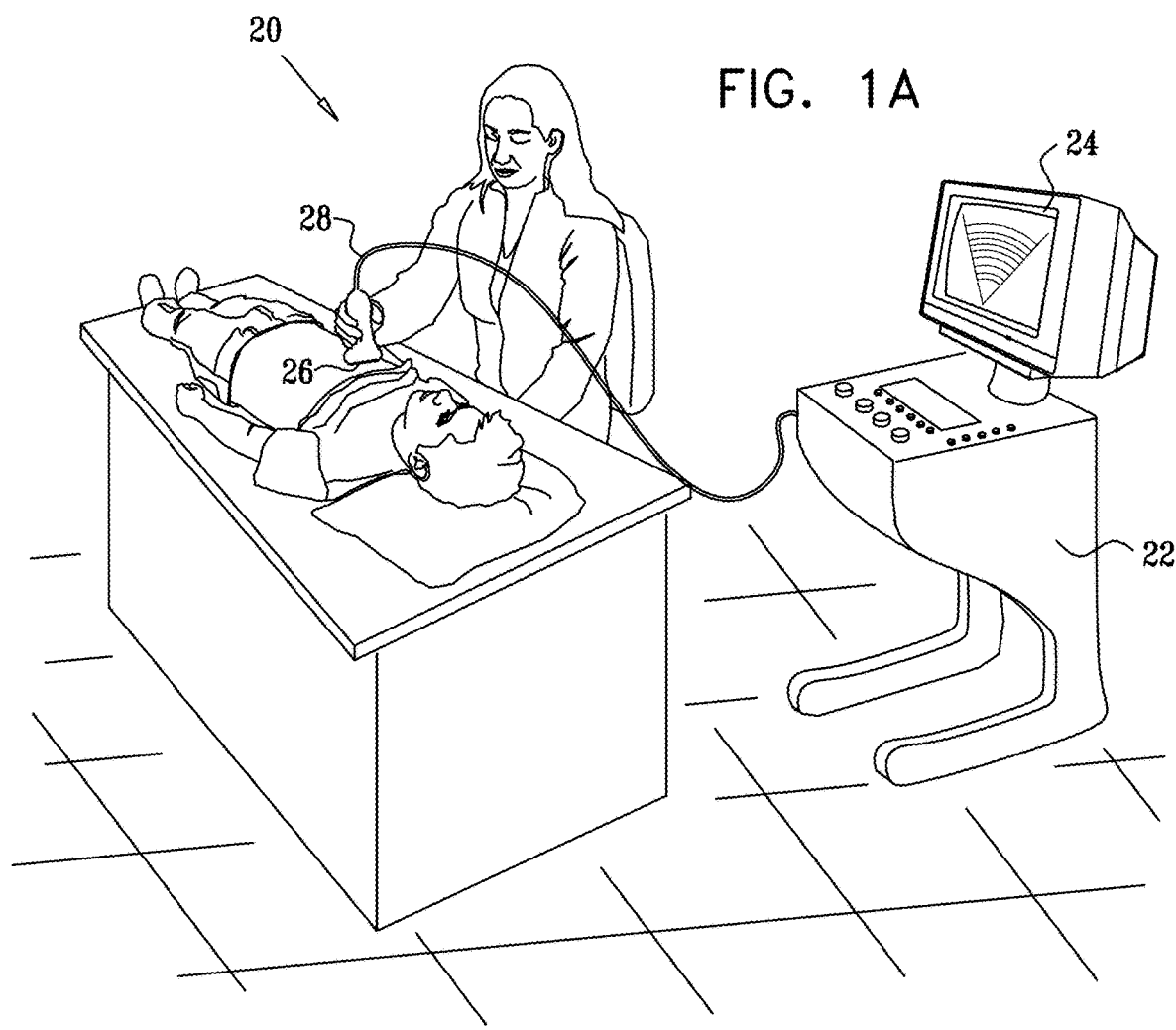
FIG. 1A is a schematic, pictorial illustration of an ultrasonic imaging system, in accordance with an embodiment of the present invention.

In broad terms, the present invention relates to methods and systems for suppressing clutter effects in ultrasonic imaging systems.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

System Description

FIG. 1A is a schematic, pictorial illustration of an ultrasonic imaging system 20, in accordance with an embodiment of the present invention.

System 20 comprises an ultrasound scanner 22 that scans target regions, e.g., organs of a patient, using ultrasound radiation. A display unit 24 displays the scanned images. A probe 26, connected to scanner 22 by a cable 28, is typically held against the imaged object, e.g., the patient body, in order to image a particular target region. Alternatively, the probe may be adapted for insertion into the imaged object, e.g., transesophageal or transvaginal imaging in medical applications. The probe transmits and receives ultrasound beams required for imaging. Probe 26 and/or scanner 22 comprise control and processing circuits for controlling probe 26 and processing the signals received by the probe.

Figure 1B:
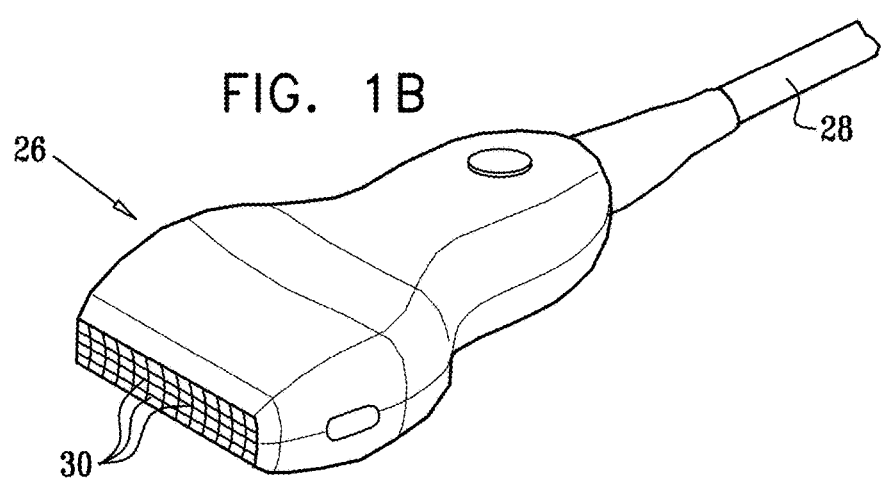
FIG. 1B is a schematic, pictorial illustration of a probe used in an ultrasonic imaging system, in accordance with an embodiment of the present invention.

FIG. 1B is a schematic, pictorial illustration of probe 26 used in imaging system 20, in accordance with an embodiment of the present invention. The probe includes an array of transducers 30, e.g., piezoelectric transducers, which may be configured to operate as a phased array. On transmission, the transducers convert electrical signals produced by scanner 22 into a beam of ultrasound radiation, transmitted into the target region. On reception, the transducers receive the ultrasound radiation reflected from the target region, and convert it into electrical signals, which are further processed by probe 26 and/or scanner 22.

The processing applied on reception typically comprises:
i) Beamforming, that is, compounding the reflected signals reaching each of the transducers in transducer array 30 and converted into electrical signals, to obtain a signal associated with an acoustic beam resulting from said reflected signals. The beam may be focused or unfocused.

When using pulsed-wave (PW) transmissions, the time delay between pulse transmission and signal reception is indicative of the distance R between the probe's surface and the spatial location within the imaged object from which the signal has been reflected (this description is accurate assuming a single reflection, without scattering or multi-path). Using the simplistic assumption of a constant speed of sound c within the medium, the time delay between pulse transmission and signal reception simply equals 2R/c. In some systems 20, the reception focus may be set to vary as a function of time since pulse transmission, so as to optimize the reception beam width along the beam path ("adaptive focusing"); and ii) Matched filtering. For example, when transmitting a pulse with a constant carrier frequency $f_c$, the matched filtering may comprise mixing the received signal with a reference signal, being a cosine signal coherently matching the frequency and phase of the transmitted signal, and applying a temporal low-pass filter to the output (mixing two pure cosine signals results in the sum of two cosine signals, one whose frequency matches the difference between the mixed signals' frequencies, and another whose frequency matches the sum of the mixed signals' frequencies; the low-pass filter discards the latter component), to obtain a matched filter output signal, referred to herein as the "real matched-filtered signal". Similarly, when transmitting a coded pulse, the complex conjugate of the transmitted signal is used as the reference signal.

Some systems also mix the received signal with a second reference signal, having the same frequency (as a function of time) as the first reference signal but shifted in phase by 90°, and apply a temporal low-pass filter to the output, to obtain a second matched filter output signal. The result of summing, for each time index, the first matched filter output signal with the second matched filter output signal multiplied by j (the square root of minus one), is referred to as the "complex I/Q signal" (the I stands for "in-phase", and the Q stands for "quadrature").

Both the real matched-filtered signal and the complex I/Q signal may be employed in a wide variety of applications. If necessary, simple transformations between the real matched-filtered signal and the complex I/Q signal are known in the art. For example, one may apply the Hilbert transform to the real matched-filtered signal, to obtain the complex I/Q signal.

Similarly, the real component of the complex I/Q signal can be used as the real matched-filtered signal. Note that the number of samples associated with the complex I/Q signal is twice as high as the number of samples associated with the real matched-filtered signal, so interpolation along the range axis may be required prior to discarding the imaginary component of the complex I/Q signal, in order to retain the information within the complex I/Q signal. The term "range axis" refers to an axis parallel to the boresight of the receive beam, whereas the term "cross-range axis" refers to any axis perpendicular to the range axis.

Also note that certain systems employ complex signals even before applying matched filtering ("complex pre-matched-filtering signals"). Such complex pre-matched-filtering signals may be produced by concurrently sampling each signal with two analog-to-digital converters, with a 90° phase difference between them (with respect to the reference signal); alternatively, the Hilbert transform may be applied to the real samples.

Both the beamforming and the matched filtering may be applied analogically, digitally, or in a combined fashion (digital processing is applied to the signal after analog-to-digital conversion). Furthermore, both beamforming and matched filtering may be performed in one or more steps, and the order between the different steps of beamforming and matched filtering may vary between different systems. For instance, matched filtering may be applied before beamforming, e.g., to the signal associated with each element of transducer array 30, or to the beamformed signal.

Additional processing applied on reception is often specific to the mode of operation of system 20. For example, when generating images of the target region morphology as a function of time, in A-mode, B-mode, or M-mode, transforming each signal sample after beamforming into a displayed videointensity may include at least one of the following steps, in any order:

i) Determining the magnitude of the signal's envelope. For complex I/Q samples, this can be performed by applying an absolute operator;

ii) Converting the signal to logarithmic units (a process referred to as "log-compression");

iii) Applying a transfer function to the signal;

iv) Replacing all values lower than a minimal value by the minimal value, and/or all values higher than a maximal value by the maximal value; and v) Scaling the signal in accordance with the displayed dynamic range.

Displaying the information may further include "scan conversion", that is, converting the data from the data acquisition coordinates to the coordinates of the display unit 24. In echocardiography, for instance, data acquisition typically employs polar coordinates, wherein a plurality of beams are transmitted at different spatial angles, all having the same phase center (the term is defined herein below), and for each such beam one or more receive beams are generated, and for each receive beam multiple samples are made, each matching a different distance from the probe's surface; conversely, the display coordinates are typically Cartesian.

Additional or different processing may be applied for Doppler-based modes of operation.

Probe Designs

Probe 26 typically comprises several dozens and up to several thousands of transducers 30. As a rule of thumb, the probe's beam width along a given axis is proportional to the ratio between the transmitted wavelength and the probe's effective size along that axis. For wideband signals, the beam width varies from one wavelength to the next, and is often estimated using a typical transmitted wavelength, e.g., the mean wavelength. The "effective size" of the probe is affected by the probe's physical dimensions, but also by the amplitudes of the weights assigned to the different transducers during beamforming (as described herein below).

The long-axis of the transducer array will be referred to as the "horizontal axis" or the "azimuth axis", whereas the short-axis of the transducer array will be referred to as the "vertical axis" or the "elevation axis". In cases where the probe is symmetrical to 90 degree rotation, one of the probe's primary axes will arbitrarily be selected as the "horizontal axis" or "azimuth axis".

In "one-dimensional probes," the transducers are arranged in a one-dimensional array, where the transducer centers are placed along a straight line or a curved line, e.g., a convex curve. "1½ dimensional probes" comprise several rows of transducers in the vertical dimension, providing a vertical sector-like beam pattern. "Two-dimensional probes" comprise a complete two-dimensional (or multi-dimensional) array of transducers, enabling control over both horizontal and vertical directional beam patterns.

Probe 26 may further comprise an acoustic lens, typically situated between the transducers and the target region. For example, in one-dimensional probes, the vertical beam-width is often adjusted by an acoustic lens.

The transducer array 30 may be stationary, or may be mechanically scanned. For example, in one-dimensional or 1½ dimensional probes, the transducer array 30 may be mechanically scanned along the vertical axis, to complement the electronic scanning made along the horizontal axis.

Beamforming

Each transmit or receive beam may be characterized by a phase center, a beam pattern, and a boresight.

The "phase center" is defined as the point along the surface of transducer array 30 from which the beam emanates. When using unfocused beams, the phase center may be ill-defined, in which case it can be defined arbitrarily, e.g., at the center of the probe.

The "beam pattern" is defined as the probe's gain as a function of spatial location. In many cases, the medium is not known a-priori, and the beam pattern is computed assuming that the propagation is within a homogeneous medium, without taking into account physical effects such as reflection, refraction, attenuation, scattering, diffraction, and the like. Note that, is certain cases, the beam pattern computed for a homogeneous medium is assumed to change only with the spatial angle (e.g., in the far-field of the receive beam, when the receive focus is constant, i.e., not adaptive), whereas in other cases the beam pattern changes as a function of time since pulse transmission as well, that is, with the distance from the probe's surface (e.g., in the near-field of the receive beam, and/or when using adaptive focusing on reception). In other cases, the beam pattern is computed for a given medium. The term "mainlobe" refers to the swath of spatial angles including the highest peak of the beam pattern, wherein if we start at the spatial angle associated with the highest probe gain and continuously scan in any direction, we remain within the mainlobe as long as we have not yet reached a null or a dip. Other gain peaks within the beam pattern are referred to as "sidelobes".

The "boresight" is a unit-vector pointing from the beam's phase center to the center of the beam's mainlobe. The "broadside" is often used as reference for the boresight, wherein the broadside is a unit-vector perpendicular to the surface of the transducer array 30, emanating from the beam's phase center.

The process of beamforming is based on applying phase shifts and/or time delays to the signals associated with each transducer 30. Phase-shift based beamforming is typically employed when the bandwidth of the transmitted signal is much lower than the carrier frequency, so that phase shifts are well defined.

To describe one common form of phase-shift based beamforming on reception, let k be the transducer index (k should go over all transducers even if the transducer array comprises more than one dimension), $s_k$ be the signal measured by transducer k (which may be analog or digital, before or after matched filtering, real or complex), $a_k$ be an apodization coefficient of transducer k on reception, $\varphi_k$ be the phase shift for transducer k on reception, and j be the square root of minus one. The beamformed signal S at time t may be computed using eq. (1):

$$S(t)=\Sigma_k a_k(t) e^{j\varphi_k(t)} s_k(t) \quad (1)$$

Alternatively, when using time-delays instead of phase shifts, where $\tau_k$ is the time-delay for transducer k, one may use eq. (2) for beamforming on reception:

$$S(t)=\Sigma_k a_k(t) s_k(t-\tau_k) \quad (2)$$

Similar equations may be used for combined time-delay and phase-shift design. Comparable equations may also be utilized on transmission.

The phase shifts $\varphi_k$ and/or the time-delays $\tau_k$ determine the beam's boresight, and also affect the beam pattern. The apodization coefficients $a_k$ are usually real, and are typically used for adjusting the beam pattern.

The apodization coefficients $a_k$ have a very similar effect to windows employed in spectral analysis, e.g., when applying discrete Fourier transform (DFT) to digital signals. Various windows known in spectral analysis, e.g., Hamming, Blackman, or Taylor windows can be employed as the apodization pattern. Based on Fourier optics principles, the far-field beam pattern as a function of spatial angle can be estimated based on applying a Fourier transform to the probe's aperture, taking into account the power distribution over the aperture on transmission, or the relative sensitivity distribution over the aperture on reception. The power distribution or sensitivity distribution are determined by the apodization coefficients.

Generally speaking, not all transducers in transducer array 30 are necessarily employed all the time. Currently used transducers are referred to as "turned-on" or "active", whereas unused transducers are "turned-off" or "inactive". Turned-off transducers are assigned an apodization coefficient 0, whereas turned-on transducers are typically assigned apodization coefficients ranging from 0 to 1. The values of the apodization coefficients over all transducers 30 ("apodization pattern") may affect the width of the beam's mainlobe as well as attributes of the beam's sidelobes (e.g., the gain ratio between the peak of the highest sidelobe and the peak of the mainlobe is referred to as the "peak-sidelobe ratio").

For unfocused beams, the receive phase shifts and/or time delays are typically set so as to make sure that the phase corrected and/or time shifted signals originating from points on a plane perpendicular to the boresight would reach all transducer elements 30 at the same time and/or phase. For focused beams, the receive phase shifts and/or time delays are typically set so as to make sure that the phase corrected and/or time shifted signals originating from the focal point would reach all transducer elements 30 at the same time and/or phase. Similar methodology is applied on transmission.

Figure 2A:
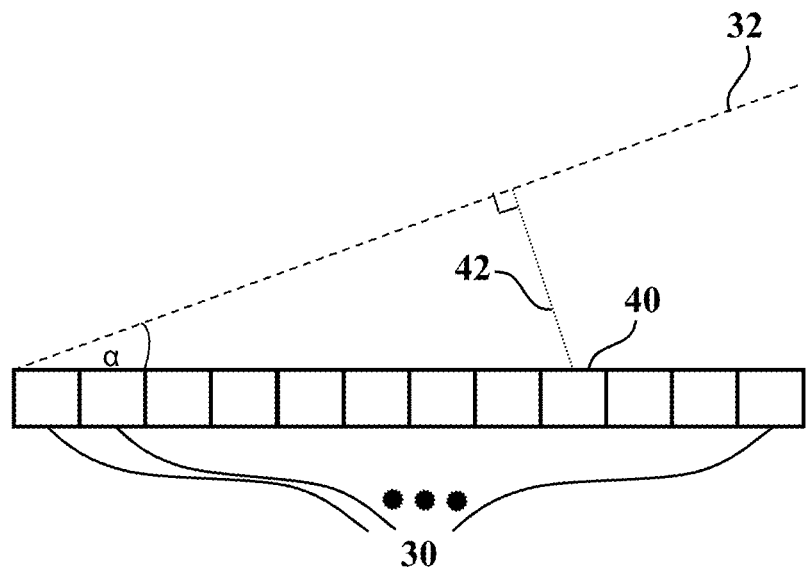
FIG. 2A is a schematic, pictorial illustration of the method for setting the phase shifts and/or time delays when generating unfocused beams using one-dimensional linear probes, in accordance with an embodiment of the present invention.

For example, for a one-dimensional linear probe, a possible scheme for setting the phase shifts and/or time delays to form unfocused receive beams is demonstrated in FIG. 2A. Let α be the angle between the surface of transducer array 30 and the required wave-front plane 32, which also equals the angle between the beam's boresight and its broadside. With phase-shift based beamforming, for a given element 40 of transducer array 30, denoted as element k, the one-way phase shift $\varphi_k$ is set to match the distance 42 from the center of element 40 to the required wave-front plane 32:

$$\varphi_k = \mathrm{mod}\left(\frac{2\pi}{\lambda} kD\sin(\alpha), 2\pi\right) \quad (3)$$

wherein λ is the transmitted wavelength, D is the distance between the centers of adjacent transducer elements, and mod is the modulus operator.

With time-delay based beamforming, for a given element 40 of transducer array 30, denoted as element k, the one-way time-delay $\tau_k$ is likewise set to match distance 42 from the center of element 40 to the required wave-front plane 32:

$$\tau_k = \frac{kD\sin(\alpha)}{c} \quad (4)$$

wherein c is the estimated speed of sound within the medium.

Figure 2B:
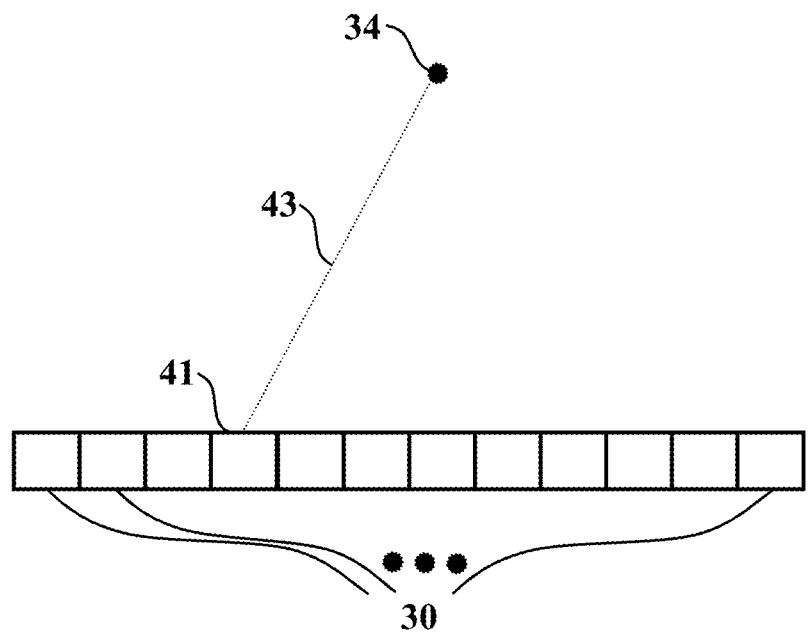
FIG. 2B is a schematic, pictorial illustration of the method for setting the phase shifts and/or time delays when generating focused beams using one-dimensional linear probes, in accordance with an embodiment of the present invention.

Similarly, for a one-dimensional linear probe, a possible scheme for setting the phase shifts and/or time delays to form focused receive beams is demonstrated in FIG. 2B. With phase-shift based beamforming, for a given element 41 of transducer array 30, denoted as element k, the one-way phase shift $\varphi_k$ follows eq. (5):

$$\varphi_k = \mathrm{mod}\left(\frac{2\pi}{\lambda} R_k, 2\pi\right) \quad (5)$$

wherein λ is the transmitted wavelength, $R_k$ is the distance 43 from the focal point 34 to the center of element k.

With time-delay based beamforming, for a given element 41 of transducer array 30, denoted as element k, the one-way time-delay $\tau_k$ follows eq. (6):

$$\tau_k = \frac{R_k}{c} \quad (6)$$

A single array of transducers 30 may generate beams with different phase centers, boresights, and beam patterns. Furthermore, some systems 20 concurrently use on reception, for a single transmitted pulse, more than one set of apodization coefficients $a_k$ and/or more than one set of phase shifts $\varphi_k$ and/or more than one set of time-delays $\tau_k$. This setting is commonly referred to as multi-line acquisition, or MLA. In MLA configurations, the beam pattern used on transmission is sometimes wider than those used on reception, so as to provide sufficient ultrasound energy to most or all of the volume covered by the different concurrent receive beams.

Further types of systems 20 use multiple concurrent beams on transmission. Examples for relevant architectures of system 20 are described herein below.

Beamforming Architectures

Beamforming on reception may be achieved using different system architectures. Two common architectures are "analog beamforming" (ABF) and "digital beamforming" (DBF). Note that some systems 20 employ ABF in one probe axis and DBF in the other.

In ABF, beamforming is applied analogically, e.g., based on eq. (1) and/or eq. (2), and sampling is applied after beamforming; however, matched filtering may be applied analogically, digitally, or in a combined fashion. The number of concurrent receive beams per transmitted beam is typically determined prior to pulse transmission. The parameters of each such receive beam are also determined prior to sampling.

In DBF, at least some beamforming steps are performed digitally. Sampling is applied either before beamforming or after some but not all beamforming steps; matched filtering may still be applied analogically, digitally, or in a combined fashion. In some configurations, an analog-to-digital converter (ADC) is assigned to each element of transducer array 30; this configuration is commonly referred to as "per-channel sampling". In other configurations, an ADC is assigned to groups of adjacent elements of transducer array 30, wherein each such group is referred to as a "sub-array". The term "sub-array" may also refer to a group of elements of transducer array 30 including a single element or to the entire transducer array. When using per-channel sampling, all beamforming steps are typically digital, whereas with sub-arrays, the beamforming may be partly digital and partly analog. DBF allows great beamforming flexibility, for instance, selecting the number of receive beams and their parameters after sampling. DBF typically involves very high data rates, necessitating relatively advanced hardware.

In both ABF and DBF, the beamforming may be performed by probe 26, scanner 22, or a combination thereof. Furthermore, beamforming parameters may change over time. For example, during scanning, the beams used on transmission and/or reception may employ varying phase centers, boresight directions, or beam patterns. In addition, with adaptive focusing, the phase-shifts and/or time-delays vary during the reception of signals for a given transmitted pulse, changing in accordance to the reception focus. Some systems 20 also synchronously change the apodization pattern with the reception focus.

In DBF, one may divide the processing associated with beamforming on reception into two groups of steps:
i) "Beamforming sample alignment"—includes applying the phase-shifts and/or time delays to the samples, and possibly applying the apodization coefficients;
ii) "Beamforming summation"—comprises summing over the samples associated with the different elements or sub-arrays of transducer array 30 (for the same range-gate), and possibly applying the apodization coefficients beforehand.

Another well-known system configuration employs a synthetic aperture, that is, the full probe aperture on transmission and/or reception is generated using multiple transmitted pulses. In some synthetic aperture systems, each transmit pulse employs a single element or a certain sub-array of transducer array 30, and the same element or sub-array is used on reception for that pulse. In other synthetic aperture systems, each transmit pulse employs a single element or a certain sub-array of transducer array 30, wherein on reception a certain element or sub-array is employed, which may not match the transmit sub-array; alternatively, the entire transducer array 30 may be used on reception. In further synthetic aperture systems, each transmit pulse employs the entire transducer array 30, but subsets of transducer array 30 are used on reception. Synthetic aperture configurations may be used for performing some or all of the beamforming steps associated with transmission, in addition to reception, after sampling. This provides great flexibility (and possibly adaptivity) in beamforming on transmission. For instance, the transmission focus may be set to vary as a function of time since pulse transmission, so as to optimize the transmission beam width along the beam path ("adaptive focusing on transmission"). Using synthetic aperture configurations, one may divide the processing associated with beamforming on reception into three groups of steps:
i) "Generation of effective receive beams"—compounding of received signals associated with multiple transmitted pulses so as to produce one or more effective receive beams, wherein the effective receive beams later undergo further processing for imaging purposes. The compounding may comprise computing linear combinations of received signals associated with multiple transmitted pulses, possibly applying phase-shifts and/or time delays to the samples (this may be seen as digital beamforming on transmission);
ii) Beamforming sample alignment; and
iii) Beamforming summation.

Alternatively, the generation of effective receive beams and the beamforming sample alignment may be performed together (the combined processing is referred to as "two-way beamforming sample alignment").

An additional system design known in the art employs multiple concurrent transmitted beams ("multiple orthogonal excitations"). On transmission, some or all elements of transducer array 30 are fed the sum of two or more signals, each associated with a different transmit beam, and each having a different waveform, e.g., a different central transmission frequency and/or different pulse encoding configuration. In these cases, each receive beam is typically generated using a specific matched filter, corresponding to one of the transmission waveforms.

A further system design known in the art is based on assigning orthogonal waveforms to different elements or sub-arrays of transducer array 30 during transmission ("orthogonal sub-array coded excitation"). Typically, at least two of the orthogonal waveforms employ the same frequency band. On reception, each element or sub-array of transducer array 30 may apply matched-filtering to more than one waveform, yielding signals associated with pairs of transmit elements/sub-arrays and receive elements/sub-arrays. As a result, the beamforming equations for both transmission and reception may be applied during processing ("two-way beamforming by processing"). This allows the flexibility of adaptively determining the transmit beam pattern, for example for adaptive focusing on transmission, in addition to reception. This configuration is described, for example, by Zheng et al., in a paper entitled "Novel Transmit Aperture for Very Large Depth of Focus in Medical Ultrasound B-Scan," IEEE Transactions on Ultrasonics, Ferroelectrics, and Frequency Control, vol. 53, 2006, pages 1079-1087.

Using orthogonal sub-array coded excitation, the processing associated with beamforming on reception is similar to that employed for synthetic aperture configurations, only that the received signals compounded are associated with multiple orthogonal waveforms, and not necessarily with multiple transmitted pulses.

Even further system designs perform adaptive focusing on transmission without using multiple orthogonal waveforms. An example for such a system design, which combines data associated with multiple transmit beams, is described in U.S. patent application 2015/0049578, by Hoctor et al., published on Feb. 19, 2015, titled "Systems and Methods for Ultrasound Retrospective Transmit Focus Beamforming."

Certain system configurations employ transmission sequences wherein multiple pulses are transmitted using the same phase center, beam pattern, and boresight, but the transmission waveform is not the same in all pulses. For each range-gate (the term is defined herein below), the samples associated with the different transmitted pulses (either after beamforming sample alignment or after beamforming) are then compounded to obtain a certain goal. Such sequences shall be referred to herein as "compounded transmission sequences".

One such compounded transmission sequence is called "pulse inversion". It employs pairs of transmission pulses, wherein the transmitted waveform of the second pulse is the complex conjugate of the transmitted waveform of the first pulse. For each range-gate, the samples for the two pulses are then coherently summed. This results in significant attenuation of linear components of the received signal, whereas non-linear components are less affected. For example, in contrast imaging, pulse inversion enhances the distinction between contrast agents and surrounding tissues, since contrast agents are characterized by significant non-linear response.

Target Region Scanning

In some modes of operation of system 20, all data acquired is associated with the same volume within the target region. This applies, for example, to various continuous wave (CW) Doppler studies in medical imaging.

In other modes of operation, different measurements made are associated with different volumes within the target region.

As mentioned herein above, with PW transmission, the time delay between pulse transmission and signal reception is indicative of the distance R between the probe's surface and the spatial location within the imaged object from which the signal has been reflected. As a result, for each receive beam, the data may be arranged in "range-gates", each associated with a different distance R. For a given receive beam, after beamforming there is a single sample for each range-gate ("beamformed range-gate"), which may be real (e.g., real sample before matched-filtering, or real matched-filtered signal) or complex (e.g., complex pre-matched-filtering signal, or complex I/Q signal). Before or during beamforming, when using per-channel sampling or sampling per sub-array, the number of samples associated with each range-gate is typically higher; for example, when the receive beam does not employ orthogonal sub-array coded excitation or synthetic aperture, the number of samples associated with each range-gate equals the number of elements of transducer array 30 used (for per-channel sampling) or the number of sub-arrays used (for sampling per sub-array). As a further example, when using orthogonal sub-array coded excitation with M orthogonal codes (which are applicable to the receive beam), after matched filtering, the number of samples associated with each range-gate equals M times the number of elements of transducer array 30 used (for per-channel sampling) or the number of sub-arrays used (for sampling per sub-array).

When multiple samples are associated with each range-gate, one can define two types of range-gate datasets: (i) "pre-aligned range-gate datasets", including for each range-gate the samples before beamforming sample alignment (and, where applicable, either before or after the generation of effective receive beams); and (ii) "aligned range-gate datasets", including for each range-gate the samples after beamforming sample alignment (where applicable, also after the generation of effective receive beams, or alternatively after two-way beamforming sample alignment), but before beamforming summation.

For a given range-gate of a given receive beam (or effective receive beam), the aligned range-gate dataset may be arranged in a D-dimensional array ("aligned range-gate array"), wherein D is the number of dimensions of transducer array 30 (for this purpose, 1½ dimensional probes are two-dimensional), and wherein the array is organized in accordance with the arrangement of transducer array 30. For a given receive beam (or effective receive beam), the aligned range-gate arrays for all associated range-gates may be stacked to obtain the "stacked aligned range-gate array", a (D+1)-dimensional array, wherein the first D dimensions correspond to the dimensions of the corresponding aligned range-gate arrays, and wherein the last dimension corresponds to the range axis, and is arranged in accordance to the distance R from the probe's surface.

With CW transmission, the time delay between pulse transmission and signal reception may be undefined, so one cannot differentiate reflections from different range-gates, and therefore there is only a single range-gate. However, using coded CW transmission, e.g., frequency modulation CW (FMCW), yields range-dependent information when applying appropriate matched filtering.

Moreover, data acquisition may comprise scanning transmit and/or receive beams over time. The scanning classically involves changing one of more of: (i) the beam's phase-center; and (ii) the beam's boresight. When using PW signals or coded CW signals on transmission, for each receive beam, one or more samples are taken for each range-gate. The data acquisition coordinates, and the arrangement of the samples, are defined accordingly. For example, in echocardiography, B-scan usually involves the phase center being kept constant, whereas the receive beam boresight is scanned to cover a two-dimensional (2D) or three-dimensional (3D) sector. The samples are thus arranged using polar coordinates (for 2D sectors) or spherical coordinates (for 3D sectors). In another example, with linear probes employed in general imaging, the typical B-scan configuration involves the phase center being scanned from side to side over time, and all receive beams are approximately perpendicular to the probe's surface. The samples are thus arranged using 2D or 3D Cartesian coordinates.

Furthermore, data acquisition may involve repeated scanning of the same target region, so as to provide time-dependent information regarding said target region. The information associated with each single scan of the target region is referred to as a "frame".

The information displayed on display unit 24 is transformed to match the display's coordinate system. In 2D imaging, the term "pixel" refers to a picture element associated with a certain volume within the imaging plane at a certain time. In 3D imaging, the term "voxel" refers to a picture element associated with a certain volume within the imaging volume at a certain time. In the context of this disclosure document, the term "pixel" will be extended to refer both to a pixel and to a voxel. For example, in M-mode scanning, used in medical imaging, the receive beam phase center and boresight are typically kept constant, and the signal is displayed as a function of distance from the probe s surface and of time. Conversely, in B-scan, different frames are usually displayed one after the other, in the order of data acquisition.

Data Acquisition Configurations for Clutter Suppression

In embodiments of the present invention, data acquisition involves:
i) Generating one or more transmit beams towards a target region. The generating each of the one or more transmit beams may involve the transmission of a PW or a CW ultrasound signal;
ii) Defining one or more reception phase centers ("defined reception phase centers"), and for each of the one or more defined reception phase centers defining one or more reception boresights ("defined reception boresights"). In some cases (typically when synthetic aperture is not in use), one or more of the defined reception phase centers may match phase centers of one or more of the one or more transmit beams. Additionally or alternatively (typically when synthetic aperture is not in use), one or more of the defined reception boresights may match boresights of one or more of the one or more transmit beams;
iii) For each of the one or more defined reception phase centers (each of the one or more defined reception phase centers separately is referred to as the "current defined reception phase center"), for each of the one or more defined reception boresights (each of the one or more defined reception boresights separately is referred to as the "current defined reception boresight"), generating two or more receive beams using the current defined reception phase center and the current defined reception boresight, wherein each of the two or more receive beams is associated with a different and distinct beam pattern;
iv) For each receive beam, producing beamformed range-gate data. Note that for un-coded CW transmitted signals, a single range-gate is typically used, corresponding to the volume covered by the entire two-way beam-pattern of the applicable transmit beam and receive beam.

In some embodiments, the two or more receive beams are associated with the same transmit beam. In other embodiments, the two or more receive beams are associated with at least two transmit beams. In further embodiments, using the synthetic aperture configuration and/or orthogonal sub-array coded excitation, the two or more receive beams may be effective receive beams.

In some embodiments, involving the transmission of PW signals, the two or more receive beams are associated with the same transmit pulse (using MLA). In other embodiments, involving the transmission of PW signals, the two or more receive beams are associated with at least two transmit pulses.

In further embodiments, one or more of ABF and DBF are used for each of the two or more receive beam.

In some embodiments, each of the two or more receive beams may employ one of the following:
i) The same carrier frequency as that of one of the one or more transmit beams;
ii) A carrier frequency being an integer multiple of the carrier frequency of one of the one or more transmit beams (this configuration is often referred to as "harmonic imaging"). For instance, the carrier frequency may be twice as high as the carrier frequency of one of the one or more transmit beams.

In certain embodiments, the producing beamformed range-gate data comprises sampling a received signal after beamforming. In other embodiments, the producing beamformed range-gate data comprises: (a) taking multiple samples for each range-gate (i.e., sampling prior to applying some or all of the beamforming steps); (b) applying one or more of: beamforming sample alignment, generation of effective receive beams, and two-way beamforming sample alignment; and (c) applying beamforming summation.

In some embodiments, the sampling is performed prior to applying matched filtering, whereas in other embodiments, the sampling is performed after applying matched filtering. In certain embodiments, the sampling is real, and in others the sampling is complex.

Clutter Suppression—Fundamental Concepts and Receive Beam Apodization Coefficients The inventor has discovered that, when multiple samples are associated with each range-gate (i.e., sampling is performed prior to applying some or all of the beamforming steps), the clutter level associated with a range-gate (the "current range-gate") and/or the probability for the current range-gate to be significantly affected by clutter may be estimated based on the following characteristics ("clutter level characteristics"):
i) When beamforming involves perfect focusing, a single reflector located at the center of a spatial volume associated with the current range-gate (clutter-free case) should result in approximately constant values over the aligned range-gate array; some variability within the aligned range-gate array may be introduced by noise as well as by differences in gain for the range-gate (e.g., in per-channel sampling, the element pattern of different elements may result in slightly different gains for each transducer element 30).

In practical cases, physical effects such as scattering along the path of the beam further increase the variability within the aligned range-gate array, even for clutter-free range-gates. However, the variability within the aligned range-gate array is typically lower for range-gates including mostly desired information than for range-gates with significant clutter contribution. This stems from the fact that signals originating from spatial angles and/or ranges far from the center of the spatial volume associated with the range-gate are not focused correctly by the beamforming process, so their beamforming phase shifts and/or time-delays are imprecise, thus increasing the variability within the aligned range-gate array.

As a result, the clutter level associated with the current range-gate and/or the probability for the current range-gate to be significantly affected by clutter may be estimated based on the variability within the corresponding aligned range-gate array ("probe spatial variability"), wherein the variability can be seen in one or more of: (a) the signal magnitude; (b) the signal phase; (c) the signal's real component; and/or (d) the signal's imaginary component; and ii) Let us define a "blob" within a two-dimensional or multi-dimensional array as a continuous spatial region with no zero-crossings within it but with zero-crossings (and/or array boundaries) at its boundaries. In this context, when the two-dimensional or multi-dimensional array is real, a zero-crossing is defined as a sign change between adjacent array elements and/or the occurrence of a value being very close to 0. When the two-dimensional or multi-dimensional array is complex, a zero-crossing is defined as a local minimum of the signal magnitude; other criteria may be added, e.g., the magnitude is lower than a threshold.

Let us examine one or more components of the stacked aligned range-gate array, or a function of one or more of said components ("stacked sample-array component"), wherein the term component here refers to the magnitude, phase, real component, and/or imaginary component.

When beamforming involves perfect focusing, a single reflector located at the center of a spatial volume associated with the current range-gate (completely clutter-free case) should result in low spatial derivatives of the stacked sample-array component along all axes, except perhaps the range axis, wherein the term "spatial derivative" may refer to any derivative, e.g., first or second derivative. The spatial derivative computation may be performed using any method known in the art, e.g., by convolving the signal with a spatial linear filtering kernel. An example for a one-dimensional kernel associated with first derivative computation: (−1 0 1); an example for a one-dimensional kernel associated with second derivative computation: (−½ 1 −½).

Similarly, blobs within the stacked sample-array component, associated with a single reflector located at the center of a spatial volume associated with the current range-gate, should have a long-axis which is almost perpendicular to the range axis.

Figure 3:
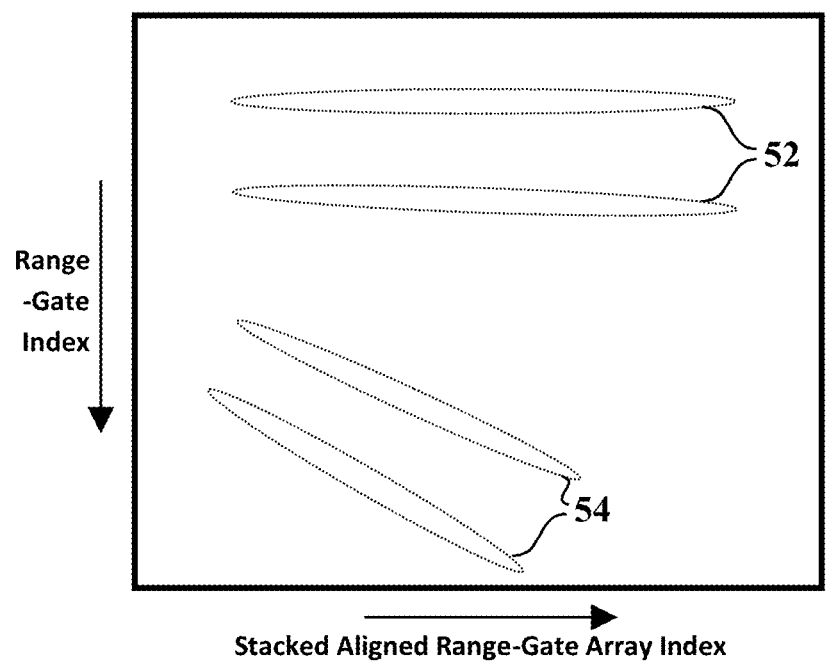
FIG. 3 is a schematic, pictorial illustration of a stacked aligned range-gate array, in accordance with an embodiment of the present invention. The horizontal axis corresponds to the index into the stacked aligned range-gate array (e.g., when using per-channel sampling, this is the index of transducer element 30), and the vertical axis corresponds to the range-gate index. The boundaries of blobs associated with strong reflectors are marked by dotted ellipses. In this example, blobs 52 result from relevant reflectors, whereas blobs 54 result from clutter reflectors.
Figure 4:
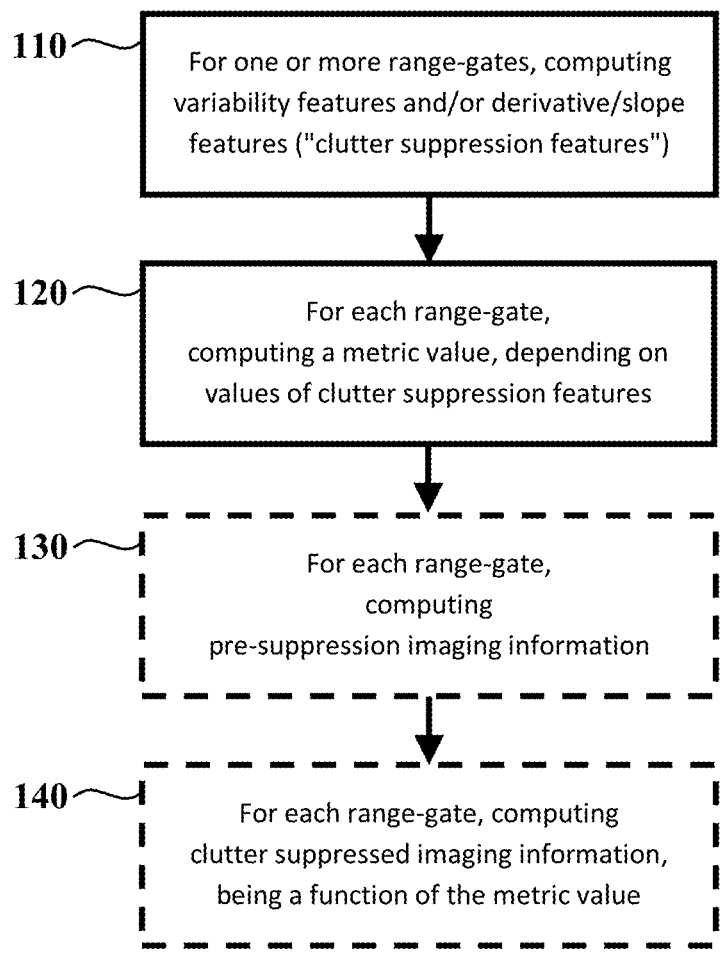
FIG. 4 is a schematic block-diagram of clutter suppression processing applied to the beamformed range-gate data, in accordance with an embodiment of the present invention. The blocks with dashed outlines, 130 and 140, are optional.
Figure 5:
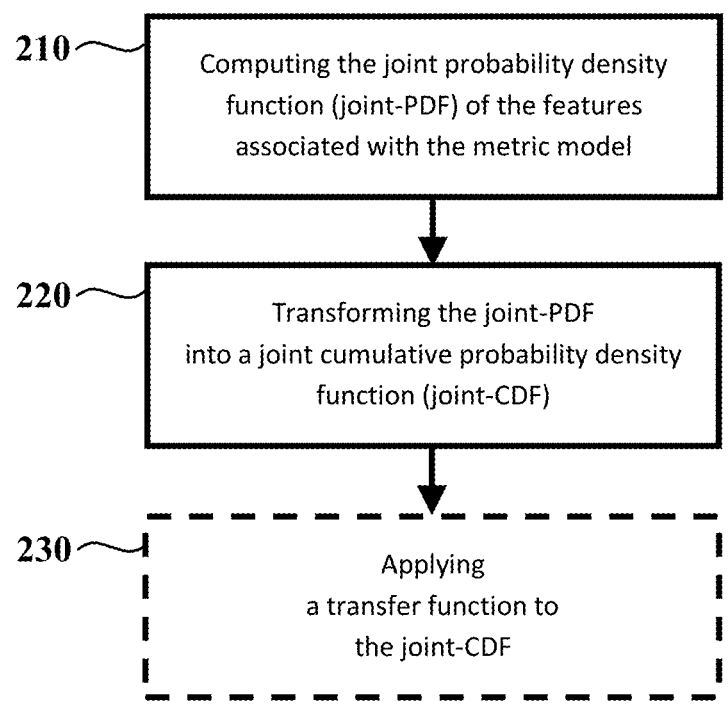
FIG. 5 is a schematic block diagram of metric model computation, in accordance with an embodiment of the present invention. The block with dashed outlines, 230, is optional.

In practical cases, even for clutter-free range-gates, physical effects such as scattering along the path of the beam, as well as the presence of multiple reflectors within range-gates, may increase the spatial derivatives of the stacked sample-array component, and/or the angle between the long-axis of blobs and the plane perpendicular to the range axis. However, the values of the spatial derivatives of the stacked sample-array component and the angle between the long-axis of blobs and the plane perpendicular to the range axis are typically lower for range-gates including mostly desired information than for range-gates significantly affected by clutter. This stems from the fact that signals originating from spatial angles and/or ranges far from the center of the spatial volume associated with the current range-gate are not focused correctly by the beamforming process, and their beamforming phase shifts and/or time-delays are imprecise. For illustration, see FIG. 3, showing a stacked aligned range-gate array. The outlines of blobs associated with strong reflectors are marked by dotted ellipses. In this example, blobs 52 result from relevant reflectors, whereas blobs 54 result from clutter reflectors.

As a result, the clutter level associated with the current range-gate and/or the probability for the current range-gate to be significantly affected by clutter may be estimated based on one or more of the following:

a. The values (for the current range-gate) of the spatial derivative of the stacked sample-array component along one or more axes other than the range axis ("stacked array spatial derivative"), referring only to the current range-gate, wherein:
  i. The spatial derivative may be any spatial derivative, e.g., first or second derivative;
  ii. The spatial derivative may be normalized in various ways. For instance, the spatial derivative normalization may match the spatial distance between adjacent elements of the stacked sample-array component along the applicable axis (e.g., range or cross-range axis). Alternatively, the spatial derivative normalization may depend on the index along the applicable axis of stacked sample-array component, e.g., the range-gate index; and
  iii. Each axis may be, but does not have to be, aligned with one of the probe's primary axes; and b. The absolute value of the angular difference between the orientation of blobs within the stacked sample-array component and the orientation of a plane perpendicular to the range axis ("blob slope"), referring only to blobs passing through the current range-gate, wherein:
  i. The blob slope may be described in terms of an angle or a spatial angle. Various coordinate systems may be employed. For example, one may employ the data acquisition coordinate system, which may be, for instance, polar, spherical, or Cartesian. Another example would be to employ the indices into the stacked sample-array component; and
  ii. The blob slope may be computed for one or more axes separately, wherein each axis may be, but does not have to be, aligned with one of the probe's primary axes. Alternatively, the blob slope may be computed in three-dimensional (or multi-dimensional) space, as the angle between the blob plane and the plane perpendicular to the range axis.

For example, when using a one-dimensional probe, the blob slope may be estimated based on the arctan of the ratio between the stacked array spatial derivative along the long-axis of the transducer array (for a linear probe, this axis matches the cross-range) and the stacked array spatial derivative along the range axis (for instance, if the arctan of said ratio is denoted $a_{ratio}$, and |•| denotes the absolute operator, the blob slope may be defined as: $1-(2/\pi)\cdot||a_{ratio}|-(\pi/2)|$). As mentioned above, any spatial derivative may be employed, e.g., first or second derivative.

When using a two-dimensional or a multi-dimensional probe, the blob slope may be similarly estimated along one or more planes, e.g., the plane defined by the range axis and the horizontal axis and/or the plane defined by the range axis and the vertical axis. Additionally or alternatively, one may further transform the estimated blob slope along two or more planes into a global slope, defined as the angle between the estimated blob plane and the range axis.

In some embodiments, the probe spatial variability for the current range-gate may be evaluated using various attributes ("variability features"), which may belong to one or more of the following attribute groups:

i) The standard deviation or variance of the aligned range-gate array associated with the current range-gate, taking into account one or more of the following components of the array's signal: magnitude, phase, real component, and/or imaginary component. Low values are associated with low probe spatial variability, and therefore low local clutter level and/or low local probability for the range-gate to be significantly affected by clutter;

ii) A certain statistic (e.g., mean, median, predefined percentile) of the spatial derivatives within the aligned range-gate array associated with the current range-gate, taking into account one or more of the following components of the array's signal: magnitude, phase, real component, and/or imaginary component. The term "spatial derivative" here may refer to any derivative, e.g., first or second derivative. When the aligned range-gate array is two-dimensional or multi-dimensional, said spatial derivatives may be in one or more axes of the aligned range-gate array, wherein each axis may be, but does not have to be, aligned with one of the probe's primary axes. Low values are associated with low probe spatial variability;

iii) A feature associated with counting zero-crossings within the aligned range-gate array associated with the current range-gate. When the aligned range-gate array is real, a zero-crossing is defined as a sign change between adjacent array elements and/or the occurrence of a value being very close to 0. When the aligned range-gate array is complex, a zero-crossing is defined as a local minimum of the signal magnitude; other criteria may be added, e.g., the magnitude is lower than a threshold. Examples for such features:
   a. The number of zero-crossings within the aligned range-gate array. Low values are associated with low probe spatial variability; and
   b. The number of zero-crossings within the aligned range-gate array, divided by the number of active transducer elements. Low values are associated with low probe spatial variability;

iv) A feature associated with estimating peak widths within the aligned range-gate array associated with the current range-gate, wherein the peak may be associated with one or more of the following components of the array's signal: magnitude, phase, real component, and/or imaginary component. When the aligned range-gate array is two-dimensional or multi-dimensional, said peak widths may be estimated along one or more axes of the aligned range-gate array, wherein each axis may be, but does not have to be, aligned with one of the probe's primary axes. For this purpose, one may use, for instance, the null-to-null peak width or the width of the peak at a certain level beneath the peak value (e.g., 3 dB peak width). Examples for such features:
   a. A certain statistic (e.g., mean, median, predefined percentile) of the peak widths within the aligned range-gate array. High values are associated with low probe spatial variability; and
   b. The width of the peak within the aligned range-gate array having the highest magnitude. High values are associated with low probe spatial variability;

v) The width of the output of the auto-correlation function applied to the aligned range-gate array associated with the current range-gate. When the aligned range-gate array is two-dimensional or multi-dimensional, said width may be estimated along one or more axes of the aligned range-gate array, wherein each axis may be, but does not have to be, aligned with one of the probe's primary axes. High values are associated with low probe spatial variability; and vi) A feature involving computing the power spectrum of the aligned range-gate array associated with the current range-gate. When the aligned range-gate array is two-dimensional or multi-dimensional, said power spectrum may be associated with spectral analysis along one or more axes of the aligned range-gate array, wherein each axis may be, but does not have to be, aligned with one of the probe's primary axes. Examples for such features:
   a. The energy ratio between a predefined group of low frequency components and a predefined group of high frequency components within the power spectrum of the aligned range-gate array. High values are associated with low probe spatial variability;
   b. The energy ratio between a predefined group of low frequency components and the total energy within the power spectrum of the aligned range-gate array. High values are associated with low probe spatial variability;
   c. The energy ratio between the spectrum element with the highest energy level and the total energy within the power spectrum of the aligned range-gate array. High values are associated with low probe spatial variability;
   d. The absolute frequency associated with the spectrum element with the highest energy level within the power spectrum of the aligned range-gate array. Low values are associated with low probe spatial variability; and
   e. The lowest frequency associated with an element of the cumulative power spectrum of the aligned range-gate array, whose energy is greater than (or equal to) a predefined constant (between 0 and 1) times the total energy within the power spectrum of the aligned range-gate array. Low values are associated with low probe spatial variability. The cumulative power spectrum of a signal is defined to be determined as follows:
      i. Compute the power spectrum of the signal;
      ii. For each absolute frequency, compound the power spectrum for the corresponding positive and negative frequencies, e.g., by averaging or taking the maximum over the two corresponding power spectrum elements, to obtain the "folded power spectrum"; and
      iii. For each absolute frequency, the cumulative power spectrum equals the sum of all folded power spectrum elements associated with lower or equal absolute frequencies.

In further embodiments, attributes ("derivative/slope features") based on the stacked array spatial derivative and/or the blob slope, providing information regarding the clutter level associated with the current range-gate and/or the probability for the current range-gate to be significantly affected by clutter, may include one or more of the following:
  i) A certain statistic (e.g., mean, weighted mean, median, certain percentile) of the stacked array spatial derivatives for the current range-gate;
  ii) A certain statistic (e.g., mean, weighted mean, median, certain percentile) of the blob slope within the stacked aligned range-gate array and/or the stacked sample-array component, referring only to blobs passing through the current range-gate;
  iii) The number of diagonal zero-crossings within the stacked aligned range-gate array and/or the stacked sample-array component, referring only to the current range-gate. A diagonal zero-crossing is defined to be detected using the following scheme:
    a. Apply zero-crossing detection to the stacked aligned range-gate array and/or the stacked sample-array component, yielding a binary matrix ("zero-crossing matrix"), where 1's appear in zero-crossing cells, and 0's appear in all other cells;
    b. Diagonal zero-crossings occur along diagonal lines of 1's within the zero-crossing matrix. For two-dimensional zero-crossing matrices, this may be detected by convolving the zero-crossing matrix with a first kernel, e.g., $$\begin{pmatrix} 1 & 0 & 0 \\ 0 & 1 & 0 \\ 0 & 0 & 1 \end{pmatrix},$$

and convolving the zero-crossing matrix with a second kernel, e.g., $$\begin{pmatrix} 0 & 0 & 1 \\ 0 & 1 & 0 \\ 1 & 0 & 0 \end{pmatrix},$$

and identifying cells for which the convolution output for at least one of the kernels equals 1.
    This number increases in the presence of high blob slopes: and
  iv) The number of diagonal zero-crossings within the stacked aligned range-gate array and/or the stacked sample-array component, divided by the number of active transducer elements, referring only to the current range-gate. This number increases in the presence of high blob slopes.

The inventor has further discovered that various variability features and/or derivative/slope features may be computed or estimated using beamformed range-gate data associated with certain receive beams. The beamformed range-gate data associated with such receive beams may also be used to provide imaging information (before clutter suppression) ("pre-suppression imaging information"). The pre-suppression imaging information may be further processed using the variability features and/or derivative/slope features, to provide clutter suppressed imaging information.

In this context, a variability feature for a range-gate is an estimate of the variability of the signal received by the different elements of transducer array 30 for the range-gate; and a derivative/slope feature for a range-gate is an estimate of a function of spatial derivatives of the signal received by the different elements of transducer array 30 for the range-gate, wherein the spatial derivatives are applied along one or more axes of the probe 26 and/or along the range axis.

In some embodiments, the beamformed range-gate data associated each receive beam may be one of the following:
  i) Used to derive one or more variability features and/or one or more derivative/slope features (such receive beams are referred to as "feature beams");
  ii) Used to acquire pre-suppression imaging information (such receive beams are referred to as "imaging beams"); or
  iii) Used to derive one or more variability features and/or one or more derivative/slope features, as well as to acquire pre-suppression imaging information (such receive beams are referred to as "suppression beams").

For example, one or more variability features and/or one or more derivative/slope features may be derived from beamformed range-gate data associated with one or more feature beams, and pre-suppression imaging information may be acquired using beamformed range-gate data associated with one or more imaging beams.

In embodiments, at least one of the feature beams and/or at least one of the suppression beams employs apodization coefficients arranged in an array whose dimensions match those of transducer array 30 ("apodization array"), wherein at least one of the apodization arrays is of one or more of the following types:
  i) A linear filter kernel, repeated one or more times over the apodization array ("linear kernel apodization array").
    In some cases, the linear filter kernel may correspond to a high-pass filter, yielding a spatial derivative (e.g., a first or a second derivative) along one or more axes.
    One possible configuration of a linear kernel apodization array involves tiling the apodization array with the linear filter kernel, wherein the tiling may be applied using various spatial shifts. For instance, for a transducer array 30 having 1 row and 9 columns, tiling the linear filter kernel (−½ 1 −½) yields three possible linear kernel apodization arrays, having different spatial shifts:
    (−½ 1 −½ −½ 1 −½ −½ 1 −½),
    (−½ −½ 1 −½ −½ 1 −½ −½ 1), and
    (1 −½ −½ 1 −½ −½ 1 −½ −½).
    As another example, for a transducer array 30 having 2 rows and 9 columns, tiling the linear filter kernel (−½ 1 −½) yields several possible linear kernel apodization arrays, one of which is:

$$\begin{pmatrix} -1/2 & 1 & -1/2 & -1/2 & 1 & -1/2 & -1/2 & 1 & -1/2 \\ -1/2 & 1 & -1/2 & -1/2 & 1 & -1/2 & -1/2 & 1 & -1/2 \end{pmatrix}.$$

Another possible configuration of a linear kernel apodization array involves initializing all values of the apodization array to 0, and copying a linear filter kernel to one or more locations within the apodization array;
  ii) A linear kernel apodization array, adjusted for each range-gate so that a set of inactive transducer elements is set to 0;
  iii) A linear apodization kernel array, multiplied element-by-element by an apodization window, e.g., a Hamming, a Blackman, or a Taylor window;

iv) A linear kernel apodization array, multiplied element-by-element by an apodization window, and further adjusted for each range-gate so that a set of inactive transducer elements is set to 0;
v) A linear kernel apodization array, adjusted for each range-gate so that a set of inactive transducer elements is set to 0, and then further adjusted so that all active transducer elements are multiplied element-by-element by an apodization window whose dimensions match those of the set of active transducer elements;
vi) An apodization array in which all elements equals either 0 of 1 ("binary apodization array");
vii) A binary apodization array, adjusted for each range-gate so that a set of inactive transducer elements is set to 0;
viii) A binary apodization array, multiplied element-by-element by an apodization window, e.g., a Hamming, a Blackman, or a Taylor window;
ix) A binary apodization array, multiplied element-by-element by an apodization window, and further adjusted for each range-gate so that a set of inactive transducer elements is set to 0; and
x) A binary apodization array, adjusted for each range-gate so that a set of inactive transducer elements is set to 0, and then further adjusted so that all active transducer elements are multiplied element-by-element by an apodization window whose dimensions match those of the set of active transducer elements.

Each of types (ii), (iii), (iv), and (v) is sometimes referred to as an "adjusted linear kernel apodization array".

In some embodiments, for at least one of the feature beams and/or at least one of the suppression beams, the set of active transducer elements per range-gate is adjusted in accordance with the apodization array parameters. For instance, when linear kernel apodization array is employed, the set of active transducer elements may be set in such a way that the active transducer elements in each range-gate would include multiple complete (i.e., without missing elements) copies of the applicable linear filter kernel.

In further embodiments, for one or more of the defined reception phase centers, for one or more of the defined reception boresights, at least one of the variability features and/or derivative/slope features for each range-gate is set to a function of the beamformed signal for that range-gate in one or more corresponding feature beams and/or one or more corresponding suppression beams ("feature function"). The feature function may be, for example, a linear combination, an exponential function, a trigonometric function, and so forth. Note that the feature function may provide information regarding the aligned range-gate array and/or the stacked aligned range-gate array even if they are not measured or computed.

In some embodiments, for one or more of the defined reception phase centers, for one or more of the defined reception boresights, one or more feature beams and/or one or more suppression beams are used to compute for each range-gate at least one derivative/slope feature providing, or being a function of, an estimate of the stacked array spatial derivatives (of any kind) along one or more cross-range axes ("required cross-range derivative"), averaged over the transducer array 30. This can be done by:
i) Setting the apodization array of the one or more feature beams and/or one or more suppression beams to a linear kernel apodization array and/or to an adjusted linear kernel apodization array, wherein the linear filter kernel associated with the linear kernel apodization array and/or the adjusted linear kernel apodization array matches the required cross-range derivative: and
ii) For each range-gate, setting the at least one derivative/slope feature to a function of one of the following:
a. A function of a linear combination of the beamformed range-gate data (for the corresponding range-gate) for the one or more feature beams and/or one or more suppression beams; or
b. A function of a linear combination of one or more components of the beamformed range-gate data (for the corresponding range-gate) for the one or more feature beams and/or one or more suppression beams, wherein each of the one or more components is one of: magnitude, phase, real component, or imaginary component.

In further embodiments, for one or more of the defined reception phase centers, for one or more of the defined reception boresights, one or more imaging beams and/or one or more feature beams and/or one or more suppression beams are used to compute for each range-gate at least one derivative/slope feature providing, or being a function of, an estimate of the stacked array spatial derivatives (of any kind) along the range axis ("required range derivative"), averaged over the transducer array 30. This can be done by one of the following methods:
i) "Derivation before combination":
a. For each of the one or more imaging beams and/or one or more feature beams and/or one or more suppression beams, for each range-gate, apply the required range derivative to the beamformed range-gate data or to the magnitude of the beamformed range-gate data; and
b. For each range-gate, set the at least one derivative/slope feature to a function of a linear combination of one of: the outputs of the previous step, or the magnitudes of the outputs of the previous step; or
ii) "Combination before derivation":
a. For each range-gate, compute a linear combination of the beamformed range-gate data or the magnitude of the beamformed range-gate data (for the corresponding range-gate) for the one or more imaging beams and/or one or more feature beams and/or one or more suppression beams; and
b. For each range-gate, set the at least one derivative/slope feature for each range-gate to a function of the output of applying the required range derivative to one of: the output of the previous step, or the magnitude of the output of the previous step.

In embodiments, each imaging beam employs apodization coefficients arranged in an apodization array, wherein at least one of imaging beams employs one or more of the following apodization array types:
i) An apodization array set to an apodization window, e.g., a Hamming, a Blackman, or a Taylor window;
ii) An apodization array initially set to an apodization window, and adjusted for each range-gate so that a set of inactive transducer elements is set to 0;
iii) An apodization array wherein, for each range-gate, all active transducer elements are set to 1 and all inactive transducer elements are set to 0; and
iv) An apodization window wherein, for each range-gate, all inactive transducer elements are set to 0, and the remaining elements are set to an apodization window whose dimensions match those of the set of active transducer elements.

In certain embodiments, for one or more of the defined reception phase centers, for one or more of the defined reception boresights, the pre-suppression imaging information for each range-gate is set to the beamformed signal for that range-gate in a corresponding imaging beam.

In other embodiments, for one or more of the defined reception phase centers, for one or more of the defined reception boresights, the pre-suppression imaging information for each range-gate is set to a linear combination of the beamformed signal for that range-gate in one or more imaging beams and/or one or more suppression beams. For example, in a case where for a given defined reception phase center and a given defined reception boresight all receive beams are suppression beams, wherein all suppression beams employ binary apodization arrays, and wherein summing the binary apodization arrays for all suppression beams (for the given defined reception phase center and the given defined reception boresight) element-by-element yields an array wherein all values equal 1, the pre-suppression imaging information for each range-gate may be set to the sum of the beamformed signal for that range-gate in all suppression beams.

As an example of an ultrasound apparatus to perform the method, the probe has a one-dimensional transducer array, and for each of the one or more defined reception phase centers and for each of the one or more defined reception boresights, one imaging beam and three feature beams are employed. The three feature beams are used to estimate for each range-gate a variability feature based on the mean of the second spatial derivatives within the aligned range-gate array associated with the range-gate. The imaging beam employs an apodization array wherein, for each range-gate, all active transducer elements are set to 1 and all inactive transducer elements are set to 0. The feature beams employ linear kernel apodization arrays, tiling the linear filter kernel ($-\frac{1}{2}$ 1 $-\frac{1}{2}$), wherein each of the feature beams uses a different spatial shift, adjusted for each range-gate so that a set of inactive transducer elements is set to 0. For each range-gate, the variability feature is set to the average of the absolute values of the beamformed signals for the three feature beams (for that range-gate).

As a further example of an ultrasound apparatus to perform the method, the probe has a one-dimensional transducer array, and for each of the one or more defined reception phase centers and for each of the one or more defined reception boresights, one imaging beam and one feature beam are employed. The feature beam is used to estimate for each range-gate a variability feature based on the mean of the second spatial derivatives within the aligned range-gate array associated with the range-gate. In this case, the mean takes into account the second spatial derivatives for only about a third of the active transducer elements within transducer array 30. The imaging beam employs an apodization array wherein, for each range-gate, all active transducer elements are set to 1 and all inactive transducer elements are set to 0. The feature beam employs a linear kernel apodization array, tiling the linear filter kernel ($-\frac{1}{2}$ 1 $-\frac{1}{2}$) using a predefined spatial shift, adjusted for each range-gate so that a set of inactive transducer elements is set to 0. For each range-gate, the variability feature is set to the absolute value of the beamformed signal of the feature beam (for that range-gate).

As an even further example of an ultrasound apparatus to perform the method, the probe has a one-dimensional transducer array, and for each of the one or more defined reception phase centers and for each of the one or more defined reception boresights, three suppression beams are employed. The suppression beams employ binary apodization arrays, adjusted for each range-gate so that a set of inactive transducer elements is set to 0. In each of the binary apodization arrays, one third of the elements are set to 1, and the 1's are equally spaced. The binary apodization arrays are thus (1 0 0 1 0 0 1 0 0 . . . ), (0 1 0 0 1 0 0 1 0 . . . ), and (0 0 1 0 0 1 0 0 1 . . . ). For each range-gate, the pre-suppression imaging information equals the coherent sum of the values of the beamformed signals for the three suppression beams (for that range-gate). The suppression beams are used to compute for each range-gate a variability feature based on the mean of the second spatial derivatives within the aligned range-gate array associated with the range-gate. The variability feature for each range-gate r, v(r), may be set to the following linear combination of the values of the beamformed signals for the three suppression beams (for that range-gate), $b_1(r)$, $b_2(r)$, and $b_3(r)$:

$$v(r) = \frac{|b_1(r) - b_2(r) - b_3(r)| + |b_2(r) - b_1(r) - b_3(r)| + |b_3(r) - b_1(r) - b_2(r)|}{N_{active}} \quad (7)$$

wherein $N_{active}$ is the number of active transducer elements for the range-gate.

Clutter Suppression Processing
Clutter Suppression Scheme

In embodiments of the present invention, the processing of the beamformed range-gate data comprises, for at least one of the one or more defined reception phase centers, for at least one of the one or more defined reception boresights:

i) Step 110: For one or more range-gates, computing one or more variability features and/or one or more derivative/slope features (the variability features and derivative/slope features are collectively referred to as "clutter suppression features"), being functions of the beamformed range-gate data associated with at least one of the two or more receive beams, wherein a clutter suppression feature provides information which is indicative, either by itself or when combined with other clutter suppression features, of the clutter level associated with the range-gate or the probability for the range-gate to be significantly affected by clutter; and ii) Step 120: For each of the one or more range-gates, computing a metric value, indicative of the of the clutter level associated with the range-gate or the probability for the range-gate to be significantly affected by clutter, wherein the metric value depends on values of one or more of the one or more clutter suppression features for the range-gate.

In some embodiments, the processing of the beamformed range-gate data further comprises, for at least one of the one or more defined reception phase centers, for at least one of the one or more defined reception boresights:

i) Step 130: For each of the one or more range-gates, computing imaging information (before clutter suppression) ("pre-suppression imaging information") for the range-gate, being a linear combination of the beamformed range-gate data associated with at least one of the two or more receive beams; and ii) Step 140: For each of the one or more range-gates, computing clutter suppressed imaging information, being a function of the corresponding pre-suppression imaging information and the corresponding metric value ("clutter suppression function").

Clutter Suppression Feature Computation (Step 110)

In embodiments of step 110, the clutter suppression features are computed using beamformed range-gate data which is one of: before, during, or after applying matched filtering.

In certain embodiments of step 110, the clutter suppression features are functions of beamformed range-gate data associated with the current range-gate only. In other embodiments of step 110, the clutter suppression features are functions of beamformed range-gate data associated with the current range-gate as well as spatially and/or temporally adjacent range-gates, wherein spatially adjacent range-gates may be associated with one or more of the following:
  i) A reception phase center equal to the current defined reception phase center;
  ii) A reception phase center different than the current defined reception phase center;
  iii) A reception boresight equal to the current defined reception boresight; and
  iv) A reception boresight different than the current defined reception boresight.

In embodiments of step 110, at least one of the clutter suppression features is derived from one or more of the clutter level characteristics.

In some embodiments of step 110, at least one of the clutter suppression features is an estimate for each range-gate of one or more of the following attributes of the corresponding aligned range-gate array:
  i) The standard deviation or variance of the aligned range-gate array associated with the current range-gate, taking into account one or more of the following components of the array's signal: magnitude, phase, real component, and/or imaginary component;
  ii) A certain statistic (e.g., mean, median, predefined percentile) of the spatial derivatives within the aligned range-gate array associated with the current range-gate, taking into account one or more of the following components of the array's signal: magnitude, phase, real component, and/or imaginary component. The term "spatial derivative" here may refer to any derivative, e.g., first or second derivative. When the aligned range-gate array is two-dimensional or multi-dimensional, said spatial derivatives may be in one or more axes of the aligned range-gate array, wherein each axis may be, but does not have to be, aligned with one of the probe's primary axes;
  iii) A feature associated with counting zero-crossings within the aligned range-gate array associated with the current range-gate. When the aligned range-gate array is real, a zero-crossing is defined as a sign change between adjacent array elements and/or the occurrence of a value being very close to 0. When the aligned range-gate array is complex, a zero-crossing is defined as a local minimum of the signal magnitude; other criteria may be added, e.g., the magnitude is lower than a threshold. Examples for such features:
    a. The number of zero-crossings within the aligned range-gate array; and
    b. The number of zero-crossings within the aligned range-gate array, divided by the number of active transducer elements;
  iv) A feature associated with estimating peak widths within the aligned range-gate array associated with the current range-gate, wherein the peak may be associated with one of the following components of the array's signal: magnitude, phase, real component, and/or imaginary component. When the aligned range-gate array is two-dimensional or multi-dimensional, said peak widths may be estimated along one or more axes of the aligned range-gate array, wherein each axis may be, but does not have to be, aligned with one of the probe's primary axes. For this purpose, one may use, for instance, the null-to-null peak width or the width of the peak at a certain level beneath the peak value (e.g., 3 dB peak width). Examples for such features:
    a. A certain statistic (e.g., mean, median, predefined percentile) of the peak widths within the aligned range-gate array; and
    b. The width of the peak within the aligned range-gate array having the highest magnitude;
  v) The width of the output of the auto-correlation function applied to the aligned range-gate array associated with the current range-gate. When the aligned range-gate array is two-dimensional or multi-dimensional, said width may be estimated along one or more axes of the aligned range-gate array, wherein each axis may be, but does not have to be, aligned with one of the probe's primary axes; and
  vi) A feature involving computing the power spectrum of the aligned range-gate array associated with the current range-gate. When the aligned range-gate array is two-dimensional or multi-dimensional, said power spectrum may be associated with spectral analysis along one or more axes of the aligned range-gate array, wherein each axis may be, but does not have to be, aligned with one of the probe's primary axes. Examples for such features:
    a. The energy ratio between a predefined group of low frequency components and a predefined group of high frequency components within the power spectrum of the aligned range-gate array;
    b. The energy ratio between a predefined group of low frequency components and the total energy within the power spectrum of the aligned range-gate array;
    c. The energy ratio between the spectrum element with the highest energy level and the total energy within the power spectrum of the aligned range-gate array;
    d. The absolute frequency associated with the spectrum element with the highest energy level within the power spectrum of the aligned range-gate array; and
    e. The lowest frequency associated with an element of the cumulative power spectrum of the aligned range-gate array, whose energy is greater than (or equal to) a predefined constant (between 0 and 1) times the total energy within the power spectrum of the aligned range-gate array. The cumulative power spectrum of a signal is defined to be determined as follows:
      i. Compute the power spectrum of the signal;
      ii. For each absolute frequency, compound the power spectrum for the corresponding positive and negative frequencies, e.g., by averaging or taking the maximum over the two corresponding power spectrum elements, to obtain the "folded power spectrum"; and
      iii. For each absolute frequency, the cumulative power spectrum equals the sum of all folded power spectrum elements associated with lower or equal absolute frequencies.

In further embodiments of step 110, at least one of the clutter suppression features is an estimate for each range-gate of one or more of the following attributes of the corresponding stacked aligned range-gate array and/or the stacked sample-array component (for the current range-gate):

i) A certain statistic (e.g., mean, weighted mean, median, certain percentile) of the stacked array spatial derivatives for the current range-gate;
ii) A certain statistic (e.g., mean, weighted mean, median, certain percentile) of the blob slope within the stacked aligned range-gate array and/or the stacked sample-array component, referring only to blobs passing through the current range-gate;
iii) The number of diagonal zero-crossings within the stacked aligned range-gate array and/or the stacked sample-array component, referring only to the current range-gate. A diagonal zero-crossing is defined to be detected using the following scheme:
   a. Apply zero-crossing detection to the stacked aligned range-gate array and/or the stacked sample-array component, yielding a binary matrix ("zero-crossing matrix"), where 1's appear in zero-crossing cells, and 0's appear in all other cells;
   b. Diagonal zero-crossings occur along diagonal lines of 1's within the zero-crossing matrix. For two-dimensional zero-crossing matrices, this may be detected by convolving the zero-crossing matrix with a first kernel, e.g., $$\begin{pmatrix} 1 & 0 & 0 \\ 0 & 1 & 0 \\ 0 & 0 & 1 \end{pmatrix},$$

and convolving the zero-crossing matrix with a second kernel, e.g., $$\begin{pmatrix} 0 & 0 & 1 \\ 0 & 1 & 0 \\ 1 & 0 & 0 \end{pmatrix},$$

and identifying cells for which the convolution output for at least one of the kernels equals 1; and
iv) The number of diagonal zero-crossings within the stacked aligned range-gate array and/or the stacked sample-array component, divided by the number of active transducer elements, referring only to the current range-gate.

In even further embodiments of step 110, at least one of the clutter suppression features is computed for each range-gate using one or more of the following:
i) A function of a linear combination of the beamformed range-gate data (for the current range-gate) for one or more of the two or more receive beams; or
ii) A function of a linear combination of one or more components of the beamformed range-gate data (for the current range-gate) for one or more of the two or more receive beams, wherein each of the one or more components is one of: magnitude, phase, real component, or imaginary component.

In other embodiments of step 110, at least one of the clutter suppression features is computed for each range-gate using one or more of the following:
i) "Derivation before combination":
   a. For one or more of the two or more receive beams, for each range-gate, apply a derivative along the range axis to the beamformed range-gate data or to the magnitude of the beamformed range-gate data, wherein the derivative may be any spatial derivative, e.g., first or second derivative; and
   b. For each range-gate, set the clutter suppression feature to a function of a linear combination of one of: the outputs of the previous step, or the magnitudes of the outputs of the previous step; or
ii) "Combination before derivation":
   a. For each range-gate, compute a linear combination of the beamformed range-gate data or the magnitude of the beamformed range-gate data (for the current range-gate) for one or more of the two or more receive beams; and
   b. For each range-gate, set the clutter suppression feature for each range-gate to a function of the output of applying a derivative along the range axis to one of: the output of the previous step, or the magnitude of the output of the previous step. The derivative may be any spatial derivative, e.g., first or second derivative.

In some embodiments, step 110 further comprises applying a correction to the computed values of the clutter suppression features ("feature correction", e.g., multiplying each computed value by a correction factor), wherein the correction for each range-gate depends on one or more of the following:
i) The spatial angle between the boresight of the transmit beam (or the effective transmit beam) and the boresight of the receive beam (or the effective receive beam). Such corrections are applicable, for instance, in systems employing MLA;
ii) The spatial angle between the receive beam's (or effective receive beam's) boresight and the broadside. Such corrections are applicable, for instance, in phased-array probes, performing digital beam steering; and
iii) The sample's distance from the probe's surface, measured along the range axis. Such corrections may be based on a model for medium related effects within the target region.

For example, for clutter suppression features whose value is linearly correlated to the local width of the mainlobe, the feature correction may involve multiplying the computed value of said clutter suppression features by the cosine of the local spatial angle between the beam's boresight and the broadside, thus compensating for the broadening of the beam mainlobe due to beam steering.

Metric Value Computation (Step 120)

In certain embodiments of step 120, the metric value is one of:
i) Indicative of the probability for the corresponding range-gate to be substantially affected by clutter effects only, i.e., essentially all its received energy originates from clutter effects;
ii) Indicative of the probability for the corresponding range-gate to be substantially unaffected by clutter effects;
iii) Indicative of the percentage of the received energy within the corresponding range-gate that originates from clutter effects;
iv) Indicative of the percentage of the received energy within the corresponding range-gate that originates from relevant information; and
v) Set to a certain constant, e.g., 0.0, if the corresponding range-gate is not significantly affected by clutter effects, and otherwise to a different constant, e.g., 1.0.

In certain embodiments of step 120, the metric value depends on values of clutter suppression features for the current range-gate only. In other embodiments, the metric value depends on values of clutter suppression features for the current range-gate as well as additional range-gates. The additional range-gates may be associated with one or more of the following:
  i) A reception phase center equal to the current defined reception phase center;
  ii) A reception phase center different than the current defined reception phase center;
  iii) A reception boresight equal to the current defined reception boresight;
  iv) A reception boresight different than the current defined reception boresight;
  v) The current frame; and
  vi) An adjacent frame.

In some embodiments of step 120, the metric value is a predefined function of the local values of one or more clutter suppression features. For example, the predefined function may be a linear function of the values of the one or more clutter suppression features. Another possible predefined function may be the result of multiplying linear functions of each of the one or more clutter suppression features.

In other embodiments of step 120, the metric value is an adaptively determined function of local or regional values of one or more clutter suppression features. Adaptively determined functions may be used to cope with medium related physical phenomena along the path of the beam, affecting the local distribution of clutter suppression feature values, even for range-gates including mostly desired information.

In certain embodiments of step 120, the following assumptions are employed for the adaptively determined function:
  i) If a range-gate can be associated with a single dominant reflector, and the clutter suppression features are defined in accordance with the clutter level characteristics, the values of the computed clutter suppression features for that range-gate are expected to depend on the spatial angle between the single dominant reflector and the beam's boresight (this assumption is referred to as the "spatial angle dependence assumption");
  ii) The prevalence of a set of values for the clutter suppression features, associated with a certain spatial angle with respect to the beam's boresight, is correlated to the beam gain at that spatial angle (this assumption is referred to as the "prevalence assumption"). If the spatial angle dependence assumption is correct, the prevalence assumption is precise when the medium within the target region is approximately homogeneous.

Additionally or alternatively, one can employ the following assumption:
  i) By definition, clutter suppression features provide information which is indicative of the local clutter level or the probability for a range-gate to be significantly affected by clutter. For each feature, one may theoretically determine whether the desired metric value, associated with the estimation of the local clutter level or the probability for the range-gate to be significantly affected by clutter, is expected to either increase or decrease with one of: (a) the feature value; or (b) a function of the feature value, e.g., the absolute value of the feature value (this assumption is referred to as the "feature trend assumption").

Given the above assumptions, the adaptively determined function for a given spatial and/or temporal region may be based on spatial and/or temporal analysis of the values of the clutter suppression features within the spatial and/or temporal region.

Accordingly, in certain embodiments of step 120, computing the metric value comprises:
  i) Computing one or more metric models, wherein each metric model is associated with a group of range-gates ("range-gate group") and one or more of the one or more clutter suppression features ("feature group"). A single range-gate group may include all range-gates, associated with all defined reception phase centers, all defined reception boresights, and all frames ("full range-gate set"). Alternatively, the full range-gate set may be divided into range-gate groups in accordance with one or more of the following:
    a. Swaths of range with respect to the probe's surface;
    b. Swaths of reception phase centers;
    c. Swaths of spatial angle between the receive beam's boresight and broadside;
    d. Swaths of spatial angle between the boresights of the transmit beam and the receive beam; and
    e. Time swaths, e.g., defined as a certain number of consecutive frames.
  Note that a range-gate group may be associated with more than one swath of the above mentioned parameters. For instance, in 2D scanning, a range-gate group may be associated with all beams for which the absolute value of the receive beam's azimuth angle is between a predefined minimal and a predefined maximal value (in this case, the range-gate group includes two separate spatial angle swaths);
  ii) For each of the one or more range-gates, setting the metric value in accordance with the value of one or more metric models, associated with the local value of the clutter suppression features.
  In certain embodiments, when more than one range-gate group is defined, the local metric value may be based on one of the following:
    a. The metric models associated with the current range-gate group; or
    b. The metric models associated with the current range-gate group and one or more spatially and/or temporally adjacent range-gate groups. For example, one may associate each model with the spatial and/or temporal center-of-mass of the range-gate group, and for each range-gate employ interpolation between the values for the different models, in accordance with the spatial location of the range-gate with respect to said centers-of-mass.

Figure 6:
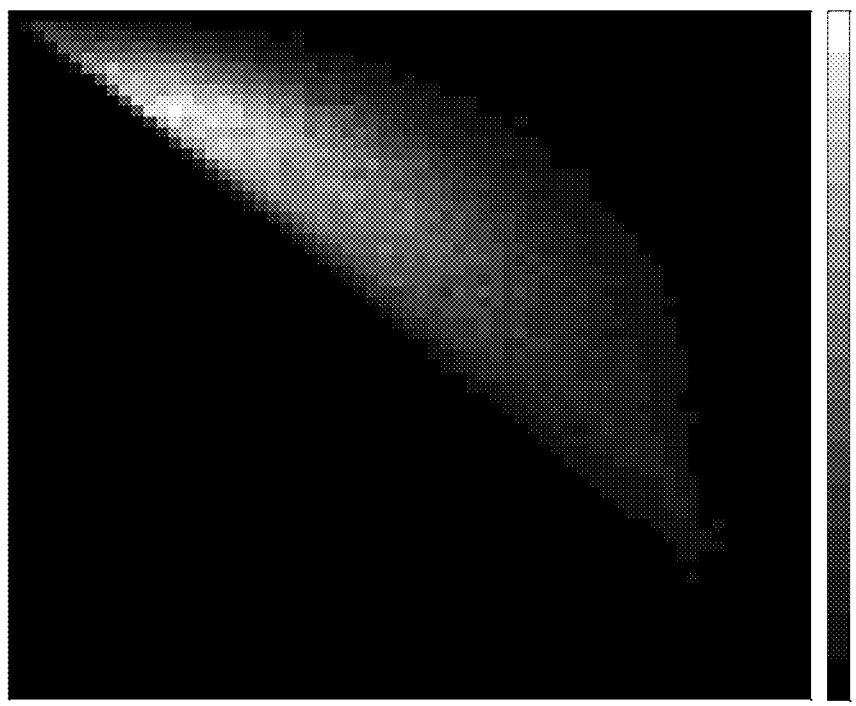
FIG. 6 is a schematic, pictorial illustration of an example for an output of step 210, the joint probability density function (joint-PDF) of two clutter suppression features associated with a metric model, in accordance with an embodiment of the present invention. The horizontal and vertical axes correspond to the values of the two features, and the local gray-level is indicative of the joint-PDF value for each pair of feature values.

In some embodiments of step 120, computing a metric model for a range-gate group comprises:
  i) Step 210: Computing the joint probability density function (joint-PDF) of the feature group associated with the metric model, taking into account only range-gates associated with the range-gate group associated with the metric model.
    The joint-PDF can be implemented, for instance, by computing a joint-histogram, and normalizing the histogram so that the sum of all its values would equal 1.0. The range of values for each axis of the joint-histogram may be predetermined or adaptively determined based on the computed range of values for the corresponding clutter suppression feature. The set of bins employed for each axis of the joint-histogram may be equally spaced or non-uniformly determined. An example for the output of step 210 for a feature group with two features can be seen in FIG. 6; and
  ii) Step 220: Transforming the joint-PDF into a joint cumulative probability density function (joint-CDF).

Figure 7:
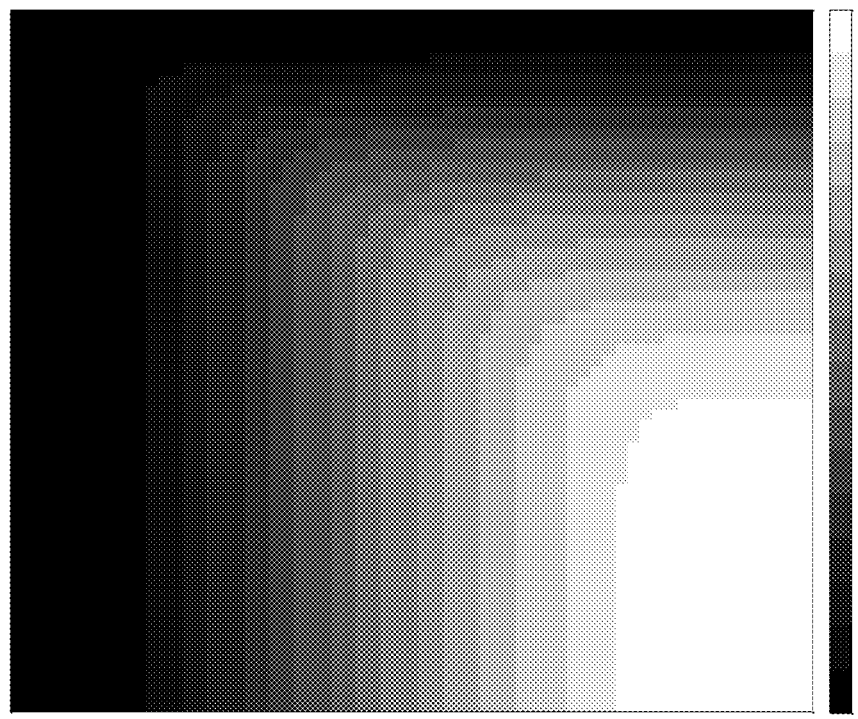
FIG. 7 is a schematic, pictorial illustration of an example for an output of step 220, the joint cumulative probability density function (joint-CDF) of two clutter suppression features associated with a metric model, in accordance with an embodiment of the present invention. The horizontal and vertical axes correspond to the values of the two features, and the local gray-level is indicative of the joint-CDF value for each pair of feature values.

The joint-CDF may use the same set of bins for each axis as the joint-PDF. The values of the joint-CDF typically range from 0.0 to 1.0. The joint-CDF computation may be performed in one of the following ways:
  a. Each element of the joint-CDF equals the sum of the values of all joint-PDF elements whose value is one of: (1) equal to or higher than the joint-PDF value for the current element; (2) equal to or lower than the joint-PDF value for the current element; (3) higher than the joint-PDF value for the current element; and (4) lower than the joint-PDF value for the current element. For options (1) and (3), the joint-CDF value increases with the local clutter level or the probability for the range-gate to be significantly affected by clutter. For options (2) and (4), the joint-CDF value decreases with the local clutter level or the probability for the range-gate to be significantly affected by clutter. This method may be explained by the prevalence assumption; and
  b. Each element of the joint-CDF equals the sum of the values of all joint-PDF elements associated with feature group values corresponding to one of: (1) equal or higher clutter level or probability for a range-gate to be significantly affected by clutter; (2) equal or lower clutter level or probability for a range-gate to be significantly affected by clutter; (3) higher clutter level or probability for a range-gate to be significantly affected by clutter; and (4) lower clutter level or probability for a range-gate to be significantly affected by clutter.
    This method may be explained by a combination of the prevalence assumption and the feature trend assumption.
    For instance, if the feature group includes two features, wherein the value of each of said features increases with the estimated local clutter level, and we define that the metric value increases with the local clutter level, each element of the joint-CDF should equal the sum of the values of all elements of the joint-PDF that correspond to lower (and optionally equal) values for each of the features in the feature group. If, for instance, we sum over joint-PDF elements corresponding to lower and equal values for each of the features, the summation can be defined by eq. (8):

$$P(a,b) = \Sigma_{n=1}^{a} \Sigma_{m=1}^{b} p(n,m) \qquad (8)$$

Wherein p is the joint-PDF and P is the joint-CDF, both of which are given as functions of the bin index for the first and second clutter suppression features in the feature group.
  An example for the output of step 220 for a feature group with two features can be seen in FIG. 7.

The output of step 220 is a metric model, that is, a matrix defining the metric value for each set of values of the feature group, over a grid defined by the joint-CDF bins. When determining the local metric value for a range-gate, based on the corresponding values for the feature group and a given metric model, one can either employ interpolation or use the nearest neighbor within the metric model.

In certain embodiments of step 120, computing the metric model for a range-gate group further comprises step 230: applying a transfer function to the joint-CDF, to obtain an adapted metric model, to be employed for metric value computation.

Figure 8:
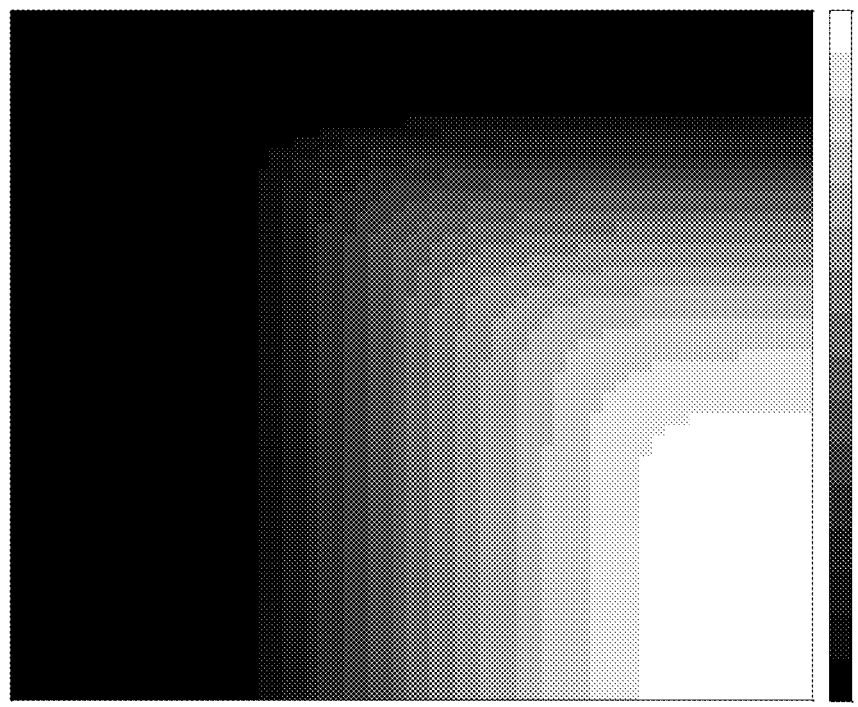
FIG. 8 is a schematic, pictorial illustration of an example for an output of step 230, the adapted metric model for two clutter suppression features, after applying an adaptive stretching transfer function to the joint-CDF, in accordance with an embodiment of the present invention. The horizontal and vertical axes correspond to the values of the two features, and the local gray-level is indicative of the adapted metric model value for each pair of feature values.

In some embodiments of step 230, the transfer function is predetermined, whereas in other embodiments the transfer function is adaptive. An example for the output of step 230 for a feature group with two features, after applying an adaptive stretching transfer function to the joint-CDF, can be seen in FIG. 8.

In embodiments of step 230, the adaptive transfer function makes use of one or more of the following parameters, derived from the joint-PDF and/or the joint-CDF (i.e., the metric model):
  i) The clutter suppression feature values associated with the joint-PDF peak, defined as one of: (a) the element within the joint-PDF whose value is highest; (b) the center-of-mass of the joint-PDF; or (c) the center-of-mass of the joint-PDF, after discarding all joint-PDF distribution modes other than the one with the highest peak and/or highest total probability.
    The joint-PDF peak corresponds to the most ubiquitous set of values for the feature group. According to the prevalence assumption, this set of values is expected to correspond to essentially clutter-free range-gates;
  ii) The clutter suppression feature values associated with the joint-PDF positive extended peak, wherein the following definitions are employed:
    a. The "long-axis of the joint-PDF" is a unit vector within the joint-PDF, pointing at the direction along which the joint-CDF value grows most rapidly with respect to the joint-PDF peak. Note that, if the feature group includes a single clutter suppression feature, the joint-PDF is one-dimensional, and the long-axis of the joint-PDF coincides with the axis of said one dimension and
    b. The "joint-PDF positive extended peak" is the element within the joint-PDF, found when starting at the joint-PDF peak and following the direction of the long-axis of the joint-PDF, until reaching an element of the joint-PDF whose value is equal to or lower than the highest joint-PDF value, multiplied by a predefined factor between 0.0 and 1.0, e.g., 0.5. If such a value is not found before reaching the joint-PDF periphery, the applicable joint-PDF element along the boundaries is employed; and
  iii) The clutter suppression feature values associated with the joint-PDF negative extended peak, wherein the following definitions are employed:
    a. The "joint-PDF negative extended peak" is the element within the joint-PDF, found when starting at the joint-PDF peak and following the direction opposite to the long-axis of the joint-PDF, until reaching an element of the joint-PDF whose value is equal to or lower than the highest joint-PDF value, multiplied by a predefined factor between 0.0 and 1.0, e.g., 0.5. If such a value is not found before reaching the joint-PDF periphery, the applicable joint-PDF element along the boundaries is employed.

In further embodiments of step 230, the adaptive transfer function involves one or more of the following, in any order:
  i) Setting all metric model elements whose value is lower than (and optionally equal to) an adaptively determined value to a certain value, e.g., the metric model value at the joint-PDF peak, wherein the adaptively determined value is one of:
    a. The metric model value at the joint-PDF peak;
    b. The metric model value at the joint-PDF positive extended peak, with a certain predefined factor; and
    c. The metric model value at the joint-PDF negative extended peak, with a certain predefined factor;

ii) Setting all metric model elements whose value is higher than (and optionally equal to) an adaptively determined value to a certain value, e.g., the metric model value at the joint-PDF peak, wherein the adaptively determined value is one of:
   a. The metric model value at the joint-PDF peak;
   b. The metric model value at the joint-PDF positive extended peak, with a certain predefined factor; and
   c. The metric model value at the joint-PDF negative extended peak, with a certain predefined factor;
iii) Linearly stretching the metric model values between a first boundary and a second boundary, wherein each of the first and second boundary is one of the following:
   a. The metric model value at the joint-PDF peak;
   b. The metric model value at the joint-PDF positive extended peak, with a certain predefined factor;
   c. The metric model value at the joint-PDF negative extended peak, with a certain predefined factor;
   d. The minimal metric model value;
   e. The maximal metric model value; and
   f. A predefined constant, e.g., 0 or 1.
   wherein the stretching may be described by eq. (9):

$$M_{out} = \begin{cases} 0 & \text{if } M_{in} \leq M_{min} \\ 1 & \text{if } M_{in} \geq M_{max} \\ \frac{M_{in} - M_{min}}{M_{max} - M_{min}} & \text{if } M_{max} > M_{in} > M_{min} \end{cases} \quad (9)$$

and wherein $M_{in}$ is the input to the transfer function, $M_{out}$ is the output of the transfer function, $M_{min}$ is the first boundary, and $M_{max}$ is the second boundary; and
iv) Applying to the metric model values one of:
   a. A polynomial function, e.g., parabolic function;
   b. An exponential function; and
   c. A logarithmic function.

In even further embodiments of step 230, the application of the transfer function is incorporated with the joint-CDF computation.

Pre-Suppression Imaging Information Computation (Step 130)

In embodiments of step 130, the pre-suppression imaging information is computed using beamformed range-gate data which is one of: before, during, or after applying matched filtering.

In certain embodiments of step 130, for one or more of the defined reception phase centers, for one or more of the defined reception boresights, the pre-suppression imaging information for each range-gate is set to the beamformed signal for that range-gate in one of the two or more receive beams.

In other embodiments of step 130, for one or more of the defined reception phase centers, for one or more of the defined reception boresights, the pre-suppression imaging information for each range-gate is set to a linear combination of the beamformed signal for that range-gate in one or more of the two or more receive beams.

Clutter Suppression Function Application (Step 140)

In some embodiments of step 140, the clutter suppressed imaging information for each range-gate only depends on the metric value for the corresponding range-gate. For example, for every range-gate, the clutter suppressed imaging information may bet set to the corresponding pre-suppression imaging information, multiplied by the corresponding metric value.

In other embodiments of step 140, the clutter suppressed imaging information for each range-gate depends on the metric value for both the corresponding range-gate and additional range-gates, each of which may be associated with one or more of the following:
   i) A reception phase center equal to the current defined reception phase center;
   ii) A reception phase center different than the current defined reception phase center;
   iii) A reception boresight equal to the current defined reception boresight;
   iv) A reception boresight different than the current defined reception boresight;
   v) The current frame; and
   vi) An adjacent frame.

In some embodiments of step 140, the clutter suppressed imaging information depends on the result of applying a spatial low-pass filter to the metric values associated with the corresponding range-gate and spatially adjacent range-gates, associated with the same defined reception phase center and the same defined reception boresight. The low-pass filter may be linear (e.g., using weighted averaging) or non-linear (e.g., using the minimum or maximum operator). This is useful, for example, when the metric values are computed based on clutter suppression features derived from real matched-filtered signal, in which case the local metric values may be affected by spatial variations associated with phase changes within the signal envelope. In such cases, the number of spatially adjacent metric values to which the low-pass filter is applied may be set so as to match the ratio between the sampling frequency on reception and the transmitted carrier frequency (i.e., the number of samples per carrier wavelength).

Additional Applications

Fundamental Concepts

The inventor has discovered that analyzing the values along the range axis ("range analysis") of certain variability features and/or derivative/slope features, computed using one or more receive beams (or effective receive beams) associated with a certain reception phase center and a certain reception boresight, provides information regarding the local speed of sound along the path of the one or more receive beams, i.e., along the range axis. The range analysis may comprise computing a derivative in range, e.g., a first derivative, of the certain variability features and/or derivative/slope features.

To explain this assertion, let us consider a receive beam passing through a medium without any sidelobe clutter, reverberations, or aberrations. The blob slope associated with a single reflector located at the center of a spatial volume associated with a range-gate is expected to be essentially zero.

Conversely, let us consider a receive beam passing through a medium causing aberrations, but not sidelobe clutter or reverberations. The blob slope associated with a single reflector located at the center of a spatial volume associated with a range-gate is expected to depend on the cumulative difference (along the path of the beam) between the actual local speed of sound and the local speed of sound assumed by the beamforming processing ("cumulative speed mismatch"). The derivative in range of the typical value (e.g., the mean value) of the blob slope per range-gate is thus expected to be correlated to the local speed of sound.

In practical cases, the physical effects along the path of the beam are more complex, but range analysis of attributes based on the blob slope is expected to provide information regarding the local speed of sound ("local speed estimate").

More generally, a local speed estimate may be obtained by range analysis of variability features and/or derivative/slope features, since some correlations may be expected between different variability features and/or different derivative/slope features.

For example, range analysis may be applied to a feature estimating for each range-gate the mean blob slope within the stacked aligned range-gate array and/or the stacked sample-array component, referring only to blobs passing through the current range-gate. Such a feature may be obtained using apodization arrays of the types defined herein above.

The local speed estimate is useful by itself. In some embodiments, the local speed estimate may be displayed to the operator on display unit 24. Additionally or alternatively, the local speed estimate may be used for beamforming, so as to improve focusing.

In further embodiments, the local speed estimate for one or more receive beams (or effective receive beams) associated with a certain reception phase center and a certain reception boresight may be employed for beamforming for the certain reception phase center and the certain reception boresight, either in the same frame or in a temporally adjacent frame. Additionally or alternatively, the local speed estimate for one or more receive beams (or effective receive beams) associated with a certain reception phase center and a certain reception boresight may be employed for beamforming for one or more receive beams (or effective receive beams) associated with a different reception phase center and/or a different reception boresight, either in the same frame or in a temporally adjacent frame.

Processing Scheme

In embodiments of the present invention, the processing of the beamformed range-gate data comprises, for at least one of the one or more defined reception phase centers, for at least one of the one or more defined reception boresights:

i) Step 310: For one or more range-gates, computing one or more variability features and/or one or more derivative/slope features (the variability features and derivative/slope features are collectively referred to as "clutter features"), being functions of the beamformed range-gate data associated with at least one of the two or more receive beams; and ii) Step 320: For each of the one or more range-gates, computing one or more of:
 a. A metric value, indicative of the clutter level associated with the range-gate or the probability for the range-gate to be significantly affected by clutter, wherein the metric value depends on values of one or more of the one or more clutter features for the range-gate; and
 b. An estimate for the local speed of sound ("local speed estimate"), being the result of analyzing the values along the range axis ("range analysis") of one or more of the one or more clutter features for the range-gate.

In certain embodiments of step 320, the range analysis may comprise computing a derivative in range, e.g., a first derivative or a second derivative, of one or more of the one or more clutter features for the range-gate.

In some embodiments, the processing of the beamformed range-gate data further comprises, for at least one of the one or more defined reception phase centers, for at least one of the one or more defined reception boresights:

i) Step 330: Performing one or more of the following:

a. Displaying to the operator on display unit 24 one or more of: the metric values, and the local speed estimates;
 b. Using the local speed estimates for beamforming;
 c. Deriving clutter suppressed imaging information, being a function of the metric values; and
 d. Using the local speed estimates for beamforming, to obtain "corrected beamformed range-gate data", and performing the following:
  i. For one or more range-gates, computing one or more variability features and/or one or more derivative/slope features (the variability features and derivative/slope features are collectively referred to as "corrected clutter features"), being functions of the corrected beamformed range-gate data associated with at least one of the two or more receive beams; and
  ii. For each of the one or more range-gates, computing one or more of:
   1. A corrected metric value, indicative of the clutter level associated with the range-gate or the probability for the range-gate to be significantly affected by clutter, wherein the corrected metric value depends on values of one or more of the one or more corrected clutter features for the range-gate; and
   2. An estimate for the local speed of sound ("corrected local speed estimate"), being a function of the result of analyzing the values along the range axis ("range analysis") of one or more of the one or more corrected clutter features for the range-gate.

In certain embodiments of step 330, the using the local speed estimates for beamforming may be associated with one or more of the following:

i) A reception phase center equal to the current defined reception phase center;
 ii) A reception phase center different than the current defined reception phase center;
 iii) A reception boresight equal to the current defined reception boresight;
 iv) A reception boresight different than the current defined reception boresight;
 v) The current frame; and
 vi) An adjacent frame.

In the above description, an embodiment is an example or implementation of the invention. The various appearances of "one embodiment", "an embodiment", "some embodiments", "certain embodiments", "other embodiments", or "further embodiments", do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment. Furthermore, it is to be understood that the invention can be carried out or practiced in various ways and that the invention can be implemented in embodiments other than the ones outlined in the description above.

Meanings of technical and scientific terms used herein are to be commonly understood as by one of ordinary skill in the art to which the invention belongs, unless otherwise defined.

The invention claimed is:

1. A method of ultrasound imaging, said method comprising:

generating one or more transmit beams towards a target region;

defining one or more reception phase centers, the one or more reception phase centers being phase centers associated with receive beams;

defining one or more reception boresights for each of the one or more defined reception phase centers;

for each of the one or more defined reception phase centers and for each of the one or more defined reception boresights, receiving a corresponding two or more receive beams using a probe (26) comprising a transducer array (30), wherein each of the two or more receive beams uses a corresponding defined reception phase center and a corresponding defined reception boresight, and wherein each of the two or more receive beams is associated with a different and distinct beam pattern;

for each receive beam, producing beamformed range-gate data; and processing the beamformed range-gate data, said processing comprising, for at least one of the one or more defined reception phase centers, for at least one of the one or more defined reception boresights:

for one or more range-gates, computing at least one of one or more variability features and one or more derivative/slope features, the one or more variability features and the one or more derivative/slope features being collectively defined as clutter suppression features, being functions of the beamformed range-gate data associated with at least one of the two or more receive beams, wherein a variability feature for a range-gate is an estimate of variability of a signal received by elements of transducer array (30) for the range-gate, and wherein a derivative/slope feature for a range-gate is an estimate of a function of spatial derivatives of the signal received by the elements of transducer array (30) for the range-gate, wherein the spatial derivatives are applied along at least one of one or more axes of the probe (26) and a range axis; and for each of the one or more range-gates, computing a metric value, wherein the metric value depends on values of one or more of the one or more clutter suppression features for the range-gate, wherein computing the metric value comprises:

computing one or more metric models, wherein each metric model is associated with a range-gate group, the range-gate group being defined as a group of range-gates, and a feature group, the feature group being defined as one or more of the one or more clutter suppression features; and for each of the one or more range-gates, setting the metric value in accordance with a value of one or more metric models, associated with a local value of the clutter suppression features, wherein computing the one or more metric models for a range-gate group comprises:

computing a joint probability density function (joint-PDF) of the feature group associated with the metric model, taking into account only range-gates associated with the range-gate group associated with the metric model;

transforming the joint-PDF into a joint cumulative density function (joint-CDF); and applying a transfer function to the joint-CDF, to obtain an adapted metric model, to be employed for metric value computation.

2. A method of ultrasound imaging, said method comprising:

generating one or more transmit beams towards a target region;

defining one or more reception phase centers, the one or more reception phase centers being phase centers associated with receive beams;

defining one or more reception boresights for each of the one or more defined reception phase centers;

for each of the one or more defined reception phase centers and for each of the one or more defined reception boresights, receiving a corresponding two or more receive beams using a probe (26) comprising a transducer array (30), wherein each of the two or more receive beams uses a corresponding defined reception phase center and a corresponding defined reception boresight, and wherein each of the two or more receive beams is associated with a different and distinct beam pattern;

for each receive beam, producing beamformed range-gate data; and processing the beamformed range-gate data, said processing comprising, for at least one of the one or more defined reception phase centers, for at least one of the one or more defined reception boresights:

for one or more range-gates, computing at least one of one or more variability features and one or more derivative/slope features, the one or more variability features and the one or more derivative/slope features being collectively defined as clutter suppression features, being functions of the beamformed range-gate data associated with at least one of the two or more receive beams, wherein a variability feature for a range-gate is an estimate of variability of a signal received by elements of transducer array (30) for the range-gate, and wherein a derivative/slope feature for a range-gate is an estimate of a function of spatial derivatives of the signal received by the elements of transducer array (30) for the range-gate, wherein the spatial derivatives are applied along at least one of one or more axes of the probe (26) and a range axis; and for each of the one or more range-gates, computing a metric value, wherein the metric value depends on values of one or more of the one or more clutter suppression features for the range-gate, wherein computing the metric value comprises:

computing one or more metric models, wherein each metric model is associated with a range-gate group, the range-gate group being defined as a group of range-gates, and a feature group, the feature group being defined as one or more of the one or more clutter suppression features; and for each of the one or more range-gates, setting the metric value in accordance with a value of one or more metric models, associated with a local value of the clutter suppression features, wherein computing the one or more metric models for a range-gate group comprises:

computing a joint probability density function (joint-PDF) of the feature group associated with the metric model, taking into account only range-gates associated with the range-gate group associated with the metric model;

transforming the joint-PDF into a joint cumulative density function (joint-CDF); and applying a transfer function to the joint-CDF, to obtain an adapted metric model, to be employed for metric value computation, wherein the transfer function depends on one or more of the following parameters, derived from at least one of the joint-PDF and the joint-CDF:

the clutter suppression feature values associated with a joint-PDF peak, defined as one of:
  (a) the element within the joint-PDF whose value is highest;
  (b) a center-of-mass of the joint-PDF; or
  (c) the center-of-mass of the joint-PDF, after discarding all joint-PDF distribution modes other than one with at least one of a highest peak and highest total probability;

the clutter suppression feature values associated with a joint-PDF positive extended peak; and the clutter suppression feature values associated with a joint-PDF negative extended peak.

3. A method of ultrasound imaging, said method comprising:

generating one or more transmit beams towards a target region;

defining one or more reception phase centers, the one or more reception phase centers being phase centers associated with receive beams;

defining one or more reception boresights for each of the one or more defined reception phase centers;

for each of the one or more defined reception phase centers and for each of the one or more defined reception boresights, receiving a corresponding two or more receive beams using a probe (26) comprising a transducer array (30), wherein each of the two or more receive beams uses a corresponding defined reception phase center and a corresponding defined reception boresight, and wherein each of the two or more receive beams is associated with a different and distinct beam pattern;

for each receive beam, producing beamformed range-gate data; and processing the beamformed range-gate data, said processing comprising, for at least one of the one or more defined reception phase centers, for at least one of the one or more defined reception boresights:

for one or more range-gates, computing at least one of one or more variability features and one or more derivative/slope features, the one or more variability features and the one or more derivative/slope features being collectively defined as clutter suppression features, being functions of the beamformed range-gate data associated with at least one of the two or more receive beams, wherein a variability feature for a range-gate is an estimate of a variability of a signal received by elements of transducer array (30) for the range-gate, and wherein a derivative/slope feature for a range-gate is an estimate of a function of spatial derivatives of the signal received by the elements of transducer array (30) for the range-gate, wherein the spatial derivatives are applied along at least one of one or more axes of the probe (26) and a range axis; and for each of the one or more range-gates, computing a metric value, wherein the metric value depends on values of one or more of the one or more clutter suppression features for the range-gate, wherein computing the metric value comprises:

computing one or more metric models, wherein each metric model is associated with a range-gate group, the range-gate group being defined as a group of range-gates, and a feature group, the feature group being defined as one or more of the one or more clutter suppression features; and for each of the one or more range-gates, setting the metric value in accordance with a value of one or more metric models, associated with a local value of the clutter suppression features, wherein computing the one or more metric models for a range-gate group comprises:

computing a joint probability density function (joint-PDF) of the feature group associated with the metric model, taking into account only range-gates associated with the range-gate group associated with the metric model; and transforming the joint-PDF into a joint cumulative density function (joint-CDF).

4. The method according to claim 3, wherein the beamformed range-gate data associated with each receive beam is one of the following:

used to derive at least one of one or more variability features and one or more derivative/slope features, such receive beams being defined as feature beams;

used to acquire pre-suppression imaging information, the pre-suppression imaging information being defined as imaging information before clutter suppression, such receive beams being defined as imaging beams; or used to derive at least one of one or more variability features and one or more derivative/slope features, as well as to acquire pre-suppression imaging information, such receive beams being defined as suppression beams.

5. The method according to claim 3, wherein beamforming sample alignment is a digital beamforming process comprising application of at least one of phase-shifts and time delays to receive beam samples, wherein beamforming summation is a digital beamforming process comprising summation over receive beam samples associated with different elements or sub-arrays of transducer array (30) for a same range-gate; wherein an aligned range-gate dataset includes for a range-gate the receive beam samples after beamforming sample alignment but before beamforming summation, wherein an aligned range-gate array is an aligned range-gate dataset arranged in an array organized in accordance with an arrangement of transducer array (30); wherein a stacked aligned range-gate array is a result of stacking aligned range-gate arrays for multiple range-gates, arranged in accordance to distance from a surface of the probe (26), wherein the multiple range-gates are associated with a same receive beam; wherein a stacked sample-array component is one or more of: (a) magnitude, (b) phase, (c) real component, and (d) imaginary component, of the stacked aligned range-gate array; and wherein at least one of the clutter suppression features is an estimate for each range-gate of one or more of the following attributes of at least one of the stacked aligned range-gate array and the stacked sample-array component for a current range-gate:

(a) a certain statistic of a stacked array spatial derivative, the stacked array spatial derivative being defined as a spatial derivative of the stacked sample-array component along one or more axes other than the range axis, referring only to the current range-gate;

(b) a certain statistic of a blob slope within the stacked sample-array component, referring only to blobs passing through the current range-gate, wherein a blob slope is an absolute value of an angular difference between an orientation of a blob within the stacked sample-array component and an orientation of a plane perpendicular to the range axis, wherein the blob is an image region that differs in a predetermined property compared to other surrounding regions of the image;

(c) a number of diagonal zero-crossings within at least one of the stacked aligned range-gate array and the stacked sample-array component, referring only to the current range-gate; and (d) the number of diagonal zero-crossings within at least one of the stacked aligned range-gate array and the stacked sample-array component, divided by a number of active transducer elements, referring only to the current range-gate.

6. The method according to claim 3, wherein at least one of the clutter suppression features is computed for each range-gate using one or more of the following methods:

a derivation before combination method comprising:

(a) For one or more of the two or more receive beams, for each range-gate, applying a derivative along the range axis to the beamformed range-gate data or to a magnitude of the beamformed range-gate data; and (b) For each range-gate, setting the clutter suppression feature to a function of a linear combination of one of: outputs of a previous step, or a magnitude of the outputs of the previous step; or a combination before derivation method comprising:

(a) For one or more of the two or more receive beams, for each range-gate, computing a linear combination of the beamformed range-gate data or the magnitude of the beamformed range-gate data; and (b) For each range-gate, setting the clutter suppression feature for each range-gate to a function of the output of applying a derivative along the range axis to one of: the output of the previous step, or the magnitude of the output of the previous step.

7. The method according to claim 3, wherein the processing the beamformed range-gate data further comprises, for at least one of the one or more defined reception phase centers, for at least one of the one or more defined reception boresights:

for each of the one or more range-gates, computing pre-suppression imaging information for the range-gate, the pre-suppression imaging information being defined as imaging information before clutter suppression and the pre-suppression imaging information being a linear combination of the beamformed range-gate data associated with at least one of the two or more receive beams; and for each of the one or more range-gates, computing clutter suppressed imaging information, the clutter suppressed imaging information being a function of the pre-suppression imaging information and of the metric value.

8. The method according to claim 7, wherein for one or more of the defined reception phase centers, for one or more of the defined reception boresights, the pre-suppression imaging information for each range-gate is set to one of:

a beamformed signal for that range-gate in one of the two or more receive beams; and a linear combination of the beamformed signal for that range-gate in one or more of the two or more receive beams.

9. The method according to claim 3, wherein at least one of the receive beams is associated with apodization coefficients arranged in an apodization array, the apodization array being defined as an array whose dimensions match those of transducer array (30), wherein at least one of the apodization arrays is of one or more of the following types:

(a) a linear kernel apodization array, being defined as a linear filter kernel repeated one or more times over the apodization array;

(b) a linear kernel apodization array, adjusted for each range-gate so that array elements corresponding to inactive transducer elements are set to 0;

(c) a linear kernel apodization array, multiplied element-by-element by an apodization window, wherein the apodization window comprises a Hamming, a Blackman, or a Taylor window;

(d) a linear kernel apodization array, multiplied element-by-element by an apodization window, and further adjusted for each range-gate so that array elements corresponding to inactive transducer elements are set to 0;

(e) a linear kernel apodization array, adjusted for each range-gate so that array elements corresponding to inactive transducer elements are set to 0, and then further adjusted so that all active transducer elements are multiplied element-by-element by an apodization window whose dimensions match those of a set of active transducer elements;

(f) a binary apodization array, being defined as an apodization array in which all elements equal either 0 or 1;

(g) a binary apodization array, adjusted for each range-gate so that array elements corresponding to inactive transducer elements are set to 0;

(h) a binary apodization array, multiplied element-by-element by an apodization window;

(i) a binary apodization array, multiplied element-by-element by an apodization window, and further adjusted for each range-gate so that array elements corresponding to inactive transducer elements are set to 0;

(j) a binary apodization array, adjusted for each range-gate so that array elements corresponding to inactive transducer elements are set to 0, and then further adjusted so that all active transducer elements are multiplied element-by-element by an apodization window whose dimensions match those of the set of active transducer elements;

(k) an apodization array set to an apodization window, wherein the apodization window comprises a Hamming, a Blackman, or a Taylor window;

(l) an apodization array initially set to an apodization window, and adjusted for each range-gate so that array elements corresponding to inactive transducer elements are set to 0;

(m) an apodization array wherein, for each range-gate, all array elements corresponding to active transducer elements are set to 1 and all array elements corresponding to inactive transducer elements are set to 0; and (n) an apodization window wherein, for each range-gate, all array elements corresponding to inactive transducer elements are set to 0, and remaining array elements are set to an apodization window whose dimensions match those of the set of active transducer elements, wherein each of types (b), (c), (d), and (e) is defined as an adjusted linear kernel apodization array.

10. The method according to claim 9, wherein either the linear kernel apodization array or the adjusted linear kernel apodization array involves one of the following:
  tiling the apodization array with the linear filter kernel, wherein the tiling may be applied using various spatial shifts; and
  initializing all values of the apodization array to 0, and copying the linear filter kernel to one or more locations within the apodization array.

* * * * *